United States Patent

Miyamoto et al.

[11] Patent Number: 5,843,606
[45] Date of Patent: Dec. 1, 1998

[54] PHENANTHRYLENEDIAMINE DERIVATIVE

[75] Inventors: Eiichi Miyamoto; Mikio Kakui; Hideo Nakamori; Yukikatsu Imanaka; Yasuyuki Hanatani, all of Osaka, Japan

[73] Assignee: Mita Industrial Co., Ltd., Osaka, Japan

[21] Appl. No.: 933,045

[22] Filed: Sep. 18, 1997

Related U.S. Application Data

[62] Division of Ser. No. 682,350, Jul. 17, 1996, abandoned.

[30] Foreign Application Priority Data

Aug. 3, 1995 [JP] Japan ..................................... 7-198809

[51] Int. Cl.⁶ .................................................. C07C 211/61

[52] U.S. Cl. ................................ 430/59; 430/56; 430/73; 430/78; 430/222; 564/308

[58] Field of Search ................................ 430/56, 59, 73, 430/78, 227

[56] References Cited

FOREIGN PATENT DOCUMENTS 5-39248   2/1993   Japan .

OTHER PUBLICATIONS

Japanese Patent Abstract No. 6346049 published Dec. 20, 1994.

Japanese Patent Abstract No. 8020770 published Jan. 23, 1996.

*Primary Examiner*—Richard L. Raymond
*Attorney, Agent, or Firm*—Beveridge, DeGrandi, Weilacher & Young, LLP

[57] ABSTRACT

In accordance with the present invention, there is provided a phenanthrylenediamine derivative represented by the general formula (1). The derivative is excellent in the electric charge transferring capability, the compatibility with a binding resin and the stability, thereby providing a photosensitive material which is highly sensitive and excellent in the durability.

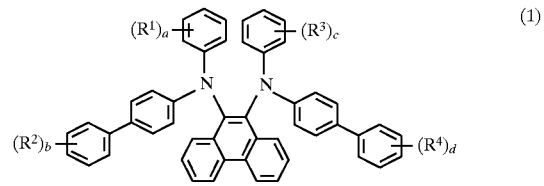

[wherein $R^1$, $R^2$, $R^3$ and $R^4$ each represent a halogen atom, an alkyl group, an alkoxy group or an aryl group; and a, b, c and d each represent an integer from 0 to 5].

12 Claims, No Drawings

PHENANTHRYLENEDIAMINE DERIVATIVE

This application is a divisional of application Ser. No. 08/682,350 filed Jul. 17, 1996, now abandoned, which application is incorporated by reference.

BACKGROUND OF THE INVENTION

The present invention relates to a novel phenanthrylenediamine derivative which is suitably used as an electric charge transferring material, particularly as a hole transferring material, in such applications as electrophotosensitive materials, solar batteries, electroluminescent devices and the like, and to an electrophotosensitive material for use in electrostatic copying machines, laser beam printers and the like.

Heretofore known as the electric charge transferring materials for use in the aforesaid applications are various organic compounds such as carbazole compounds, oxadiazole compounds, pyrazoline compounds, hydrazone compounds, stilbene compounds, phenylenediamine compounds and benzidine compounds.

These electric charge transferring materials are generally used in a state where they are dispersed in a layer of a suitable binding resin. Typically used as an electrophotosensitive material, for example, are a single-layer organic photosensitive material comprising any of the aforesaid electric charge transferring materials dispersed in a binding resin along with an electric charge generating material, and a multi-layer organic photosensitive material comprising an electric charge transferring layer containing any of the aforesaid electric transferring materials and an electric charge generating layer containing an electric charge generating material. These organic photosensitive materials are advantageous in that they are easier to produce than inorganic photosensitive materials using inorganic semiconductor materials and are allowed a wide choice for the electric charge generating material, the electric charge transferring material, the binding resin and like materials thereof, thereby offering a higher flexibility in performance design thereof.

Among the aforesaid electric charge transferring materials, an exemplary one is a m-phenylenediamine derivative represented by the following general formula:

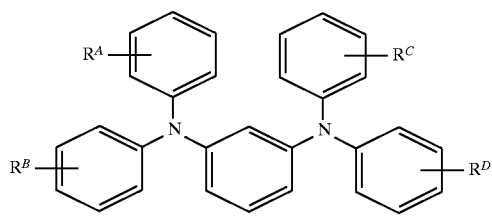

[wherein $R^A$, $R^B$, $R^C$ and $R^D$ are the same or different and each represents a hydrogen atom, a halogen atom, an alkyl group optionally having a substituent, an alkoxy group optionally having a substituent, or an aryl group optionally having a substituent].

The m-phenylenediamine derivative is highly compatible with the binder resin and excellent in the electric charge transferring capability. However, the m-phenylenediamine derivative suffers an insufficient stability, and is liable to deteriorate or decompose particularly when it is rendered highly reactive in a singlet excited state by light irradiation. This is because electrons at the HOMO (highest occupied molecular orbital) level involved in hole transfer are localized in 4- and 6-position carbon atoms of a benzene ring of the main skeleton thereof, thereby enhancing the chemical reactivity at the 4- and 6-positions of the benzene ring.

For this reason, when an electrophotosensitive material employing the m-phenylenediamine derivative as an electric charge transferring material is repeatedly used, i.e., when the electrophotosensitive material is repeatedly subjected to a process sequence of charging, light exposure and charge removal, the m-phenylenediamine derivative undergoes a photochemical reaction to produce deterioration products, which causes a decrease in the sensitivity of the photosensitive material and an increase in the charge level thereof. This results in an insufficient durability of the photosensitive material.

Japanese Unexamined Patent No. 5-39248 (1993) discloses a phenanthrylenediamine derivative including, instead of the benzene ring of the main skeleton of the phenylenediamine derivative, a phenanthrene ring having a quenching effect for promoting the deactivation from its photo-excited state, as represented by the following general formula (4):

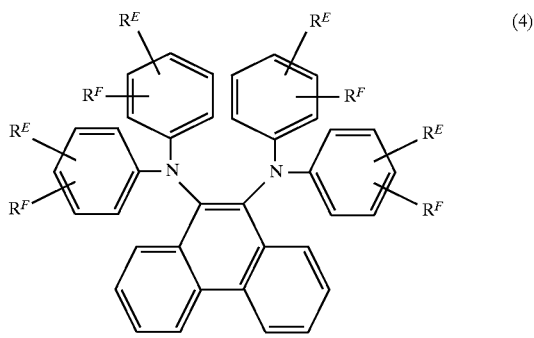

[wherein $R^E$ and $R^F$ are the same or different and each represents a hydrogen atom, a lower alkyl group, a lower alkoxy group or a halogen atom].

However, the derivative (4) does not have a practically sufficient compatibility with a binding resin to be used for a photosensitive layer, thereby causing crystallization when used for an electrophotosensitive material.

SUMMARY OF THE INVENTION

It is a principal object of the present invention to provide a novel electric charge transferring material which is excellent in the electric charge transferring capability, the compatibility with a binding resin and the stability.

It is another object of the present invention to provide an electrophotosensitive material which uses the electric charge transferring material and is excellent in the sensitivity and the durability.

In expectation that the stability of a material could be improved by employing, instead of phenyl groups respectively bonded to two nitrogen atoms of the aforesaid phenanthrylenediamine derivative, biphenyl groups which have a quenching effect and provide an improved compatibility with a binding resin, the inventors of the present invention attempted a molecular design of a phenanthrylenediamine derivative as a novel compound. As a result, the present invention has been achieved to provide a compound which has a phenanthrene ring substituted at 9- and 10-positions thereof with two nitrogen atoms each having at least one biphenyl group bonded thereto, i.e., a phenanthrylenediamine derivative represented by the general formula (1):

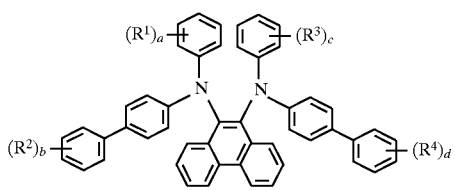

(1)

[wherein $R^1$, $R^2$, $R^3$ and $R^4$ are the same or different and each represents a halogen atom, an alkyl group optionally having a substituent, an alkoxy group optionally having a substituent, or an aryl group optionally having a substituent; and a, b, c and d are the same or different and each represents an integer from 0 to 5].

Findings imply as follows:

(a) Since electrons at the HOMO level are distributed throughout a molecule of the phenanthrylenediamine derivative along the biphenyl structures, the HOMO-level electrons are present in a larger area in the molecule than the m-phenylenediamine derivative to improve the mobility of electric charge. Therefore, the phenanthrylenediamine derivative has an improved electric charge transferring capability.

(b) Since the localization of the HOMO-level electrons is eliminated as described above, the electron distribution becomes planar. Where the phenanthrylenediamine derivative (electric charge transferring material) is incorporated in a photosensitive layer along with an electric charge generating material, a synergistic effect with the electric charge generating material, i.e., an action for deriving an electric charge (particularly, a hole) generated by the electric charge generating material, is enhanced to improve the efficiency of electric charge generation of the electric charge generating material. Thus, the sensitivity of the photosensitive material can be improved.

(c) The non-localization of the HOMO-level electrons eliminates a chemically highly reactive area within the molecule which may otherwise locally appear due to the localization of the electrons (in the case of the m-phenylenediamine derivative, such an area appears in the benzene ring at the center of the molecule thereof). This effect along with the quenching effect offered by the phenanthrene ring and the biphenyl ring allows the phenanthrylenediamine derivative to have an improved stability particularly under light irradiation.

(d) The planar electron distribution causes the structure of the molecule itself to become planar, resulting in a tendency toward a reduced compatibility with the binding resin. However, since rotational movement is permitted at σ-bonds in the biphenyl groups of the derivative, excessive planarization of the molecule thereof is suppressed. Therefore, the phenanthrylenediamine derivative has a practically sufficient compatibility with the binding resin.

According to another aspect of the present invention, there is provided an electrophotosensitive material which comprises a photosensitive layer formed on a conductive substrate and containing the phenanthrylenediamine derivative represented by the general formula (1).

DETAILED DESCRIPTION OF THE INVENTION

In the phenanthrylenediamine derivative represented by the general formula (1), examples of the halogen atom for $R^1$, $R^2$, $R^3$ and $R^4$ include a fluorine atom, a chlorine atom, a bromine atom and an iodine atom.

Examples of the alkyl group for $R^1$, $R^2$, $R^3$ and $R^4$ include lower alkyl groups having 1 to 6 carbons such as a methyl group, an ethyl group, a n-propyl group, an isopropyl group, a n-butyl group, an isobutyl group, a s-butyl group, a t-butyl group, a pentyl group and a hexyl group.

Examples of the alkoxy group for $R^1$, $R^2$, $R^3$ and $R^4$ include a methoxy group, an ethoxy group, an isopropoxy group, a butoxy group, a t-butoxy group and a hexyloxy group.

Examples of the aryl group for $R^1$, $R^2$, $R^3$ and $R^4$ include a phenyl group, a biphenyl group, a naphthyl group, an anthryl group, a phenanthryl group and an o-terphenyl group.

Examples of the substituents with which the alkyl group, the alkoxy group and the aryl group are optionally substituted include alkyl groups, halogen atoms and alkoxy groups as described above.

The numbers of the groups $R^1$, $R^2$, $R^3$ and $R^4$ defined by characters a, b, c and d, respectively, in the general formula (1) may be selected from 1 to 5. If the number a, b, c or d is 2 or greater, the groups $R^1$, $R^2$, $R^3$ or $R^4$ may be different from each other.

More specific examples of the phenanthrylenediamine derivative (1) of the present invention include a phenanthrylenediamine derivative having a biphenyl group and a phenyl group bonded to each of the two nitrogen atoms thereof as represented by the general formula (2):

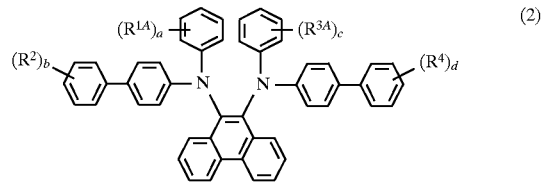

(2)

[wherein $R^{1A}$ and $R^{3A}$ are the same or different and each represents a halogen atom, an alkyl group optionally having a substituent, or an alkoxy group optionally having a substituent; $R^2$ and $R^4$ are the same or different and each represents a halogen atom, an alkyl group optionally having a substituent, an alkoxy group optionally having a substituent, or an aryl group optionally having a substituent; and a, b, c and d are the same or different and each represents an integer from 0 to 5], and a phenanthrylenediamine derivative having two biphenyl groups bonded to each of the two nitrogen atoms thereof as represented by the general formula (3):

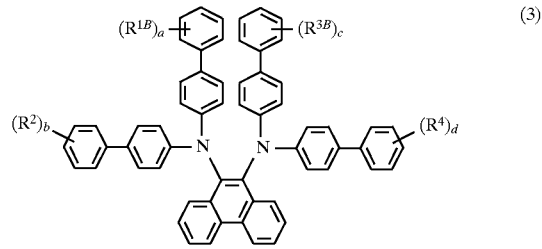

(3)

[wherein $R^{1B}$, $R^2$, $R^{3B}$ and $R^4$ are the same or different and each represents a halogen atom, an alkyl group optionally having a substituent, an alkoxy group optionally having a substituent, or an aryl group optionally having a substituent; and a, b, c and d are the same or different and each represents an integer from 0 to 5].

In terms of the compatibility with the binding resin, it is preferred that all the substituents bonded to the nitrogen atoms of the phenanthrylenediamine derivative are not the same. More specifically, the phenanthrylenediamine derivative is preferably such that two of the four substituents bonded to the nitrogen atoms are phenyl groups and the remaining two are biphenyl groups, or such that two of them are biphenyl groups and the remaining two are terphenyl groups.

More specific examples of the phenanthrylenediamine derivative represented by the general formula (2) include, though not limited thereto, compounds represented by the formulae (2-1) to (2-8):

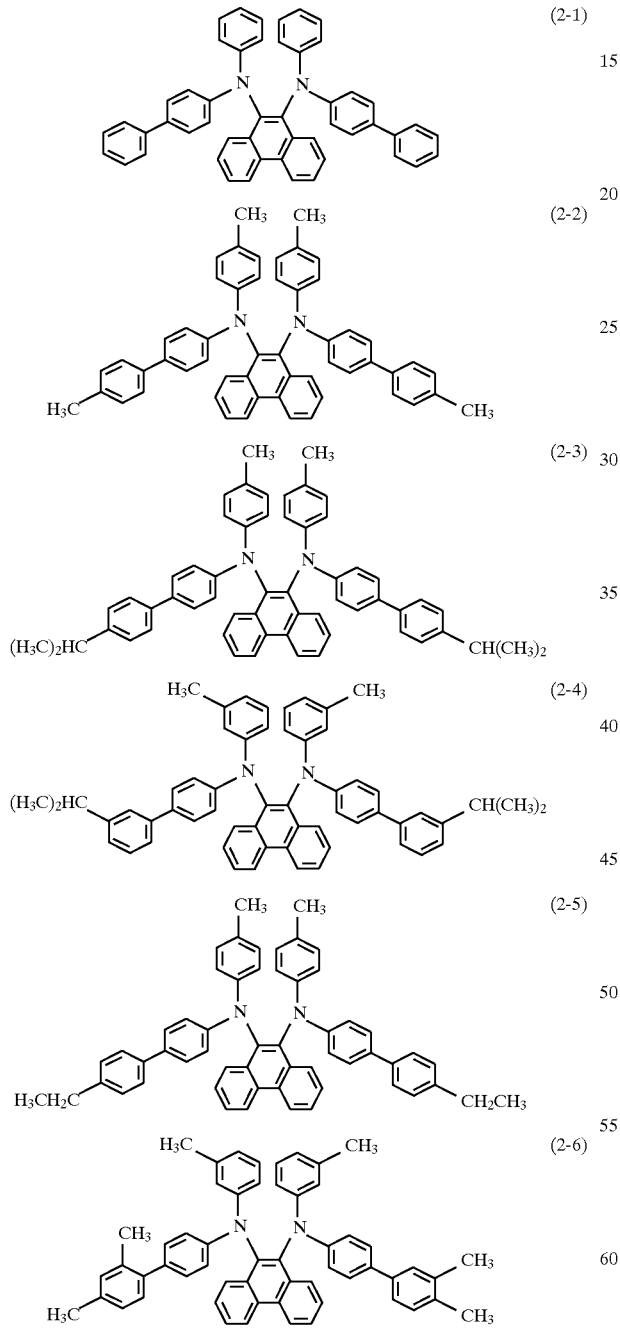

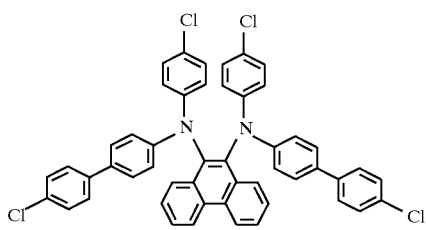

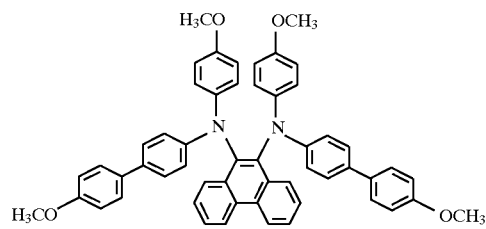

More specific examples of the phenanthrylenediamine derivative represented by the general formula (3) include, though not limited thereto, compounds represented by the formulae (3-1) to (3-11)

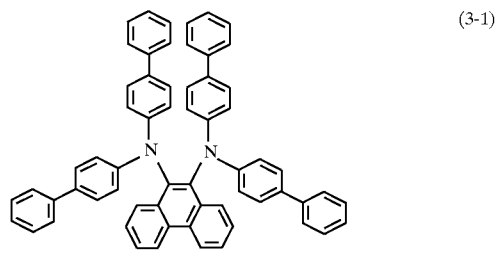

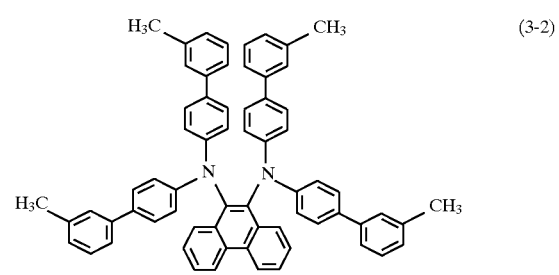

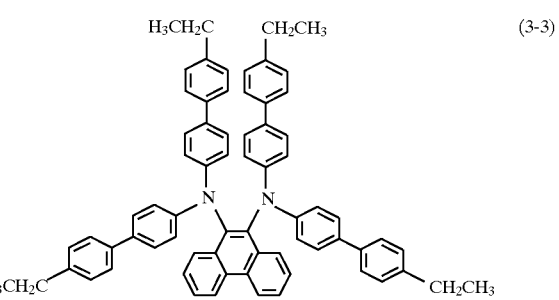

-continued

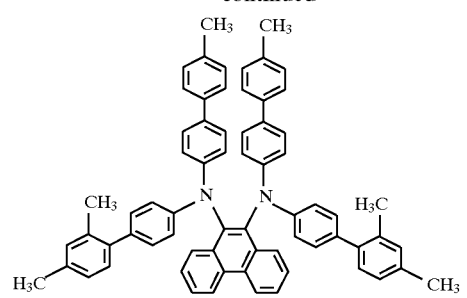 (3-4)

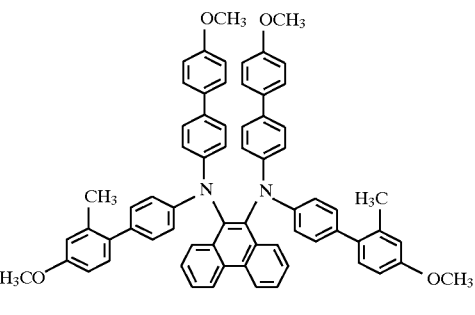 (3-5)

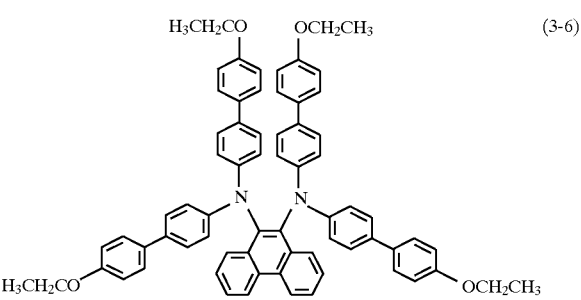 (3-6)

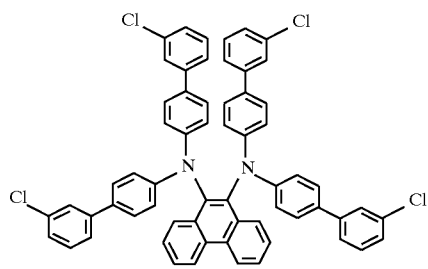 (3-7)

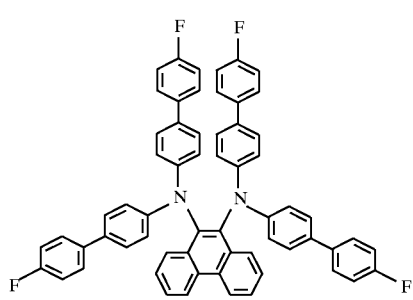 (3-8)

-continued

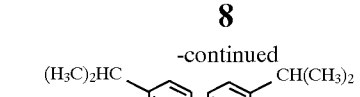 (3-9)

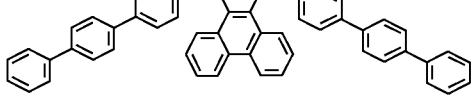 (3-10)

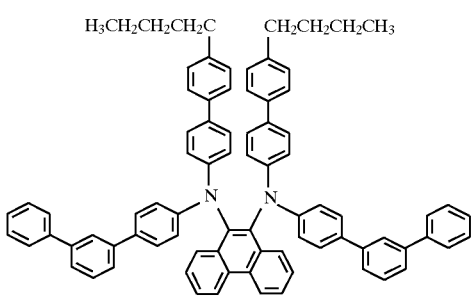

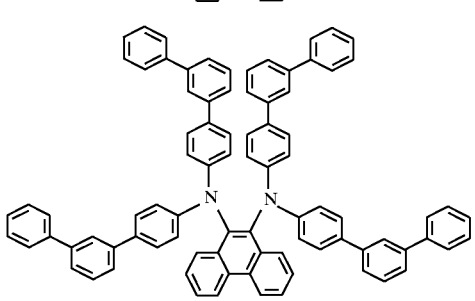 (3-11)

The phenanthrylenediamine derivative of the present invention can be synthesized by various methods.

For example, a phenanthrylenediamine derivative which has four biphenyl groups bonded to two nitrogen atoms and each having the same substituent as represented by the general formula (31) is synthesized by the following reaction scheme:

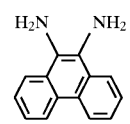

+

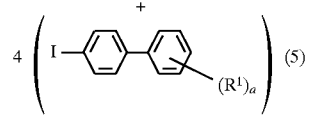 (5)

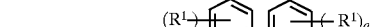

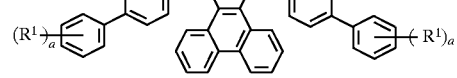

(31)

[wherein $R^1$ and a are the same as described above].

Specifically, 9,10-phenanthrylenediamine and a 4-iodobiphenyl derivative in a molar ratio of 1:4 are mixed with copper powder, copper oxide or a copper halide, and allowed to react in the presence of a basic substance to give the phenanthrylenediamine derivative (31).

A phenanthrylenediamine derivative represented by the general formula (32) is synthesized by the following reaction scheme:

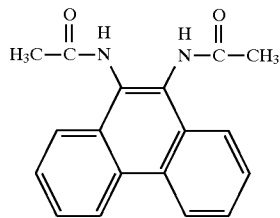

+

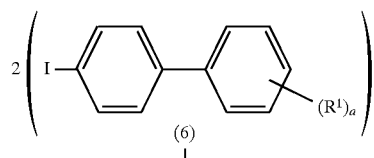

(6)

↓

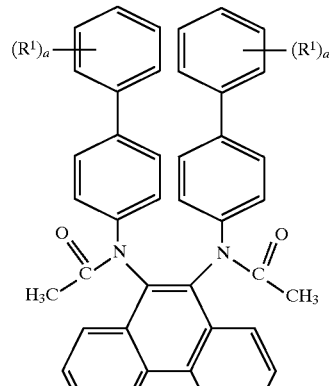

(7)

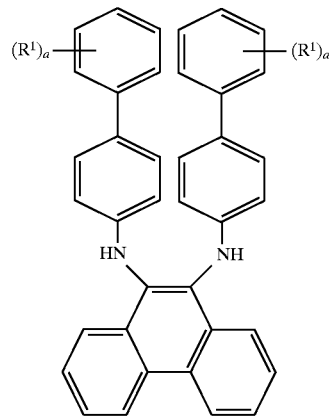

(8)

+

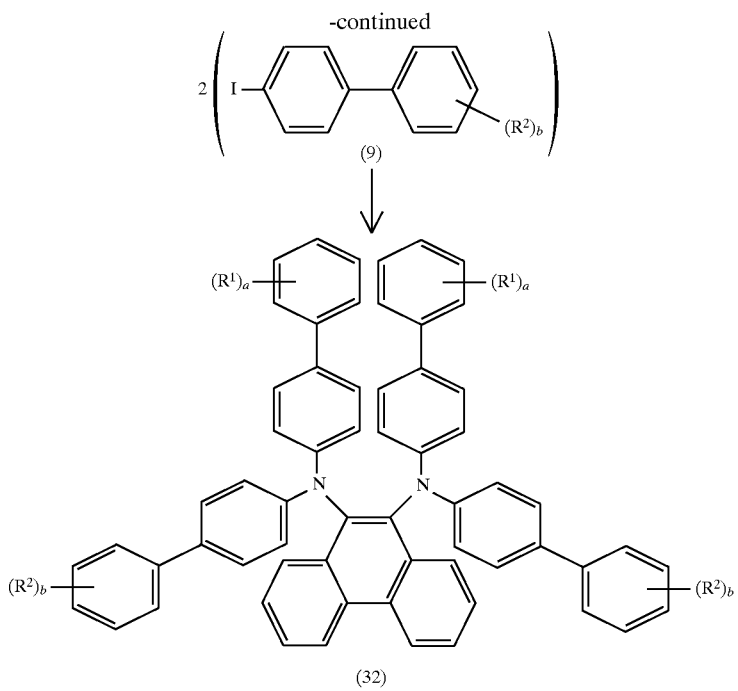

[wherein $R^1$, $R^2$ a and b are the same as described above].

Specifically, N,N'-diacetyl-9,10-phenanthrylenediamine and a 4-iodobiphenyl derivative (6) in a molar ratio of 1:2 are mixed with copper, copper oxide or a copper halide, and allowed to react in the presence of a basic substance to give an intermediate reaction product (7). In turn, the intermediate reaction product (7) is allowed to react in a suitable solvent containing hydrochloric acid to give a deacetylated intermediate product (8), which is then allowed to react with a 4-iodobiphenyl derivative (9) in a molar ratio of 1:2 in the same manner as described above.

Further, a phenanthrylenediamine derivative represented by the general formula (21) is synthesized by the following reaction scheme:

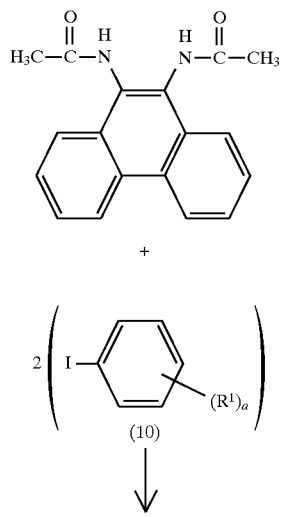

-continued

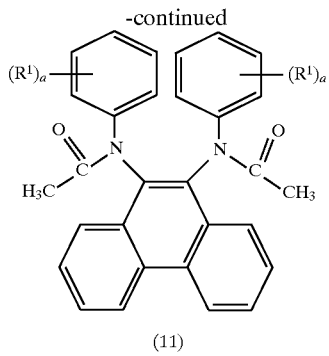

(11)

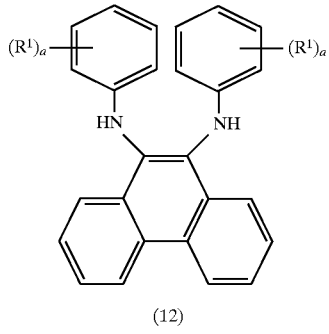

(12)

+

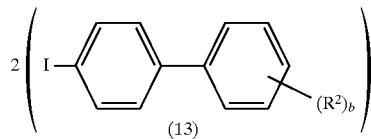

(13)

↓

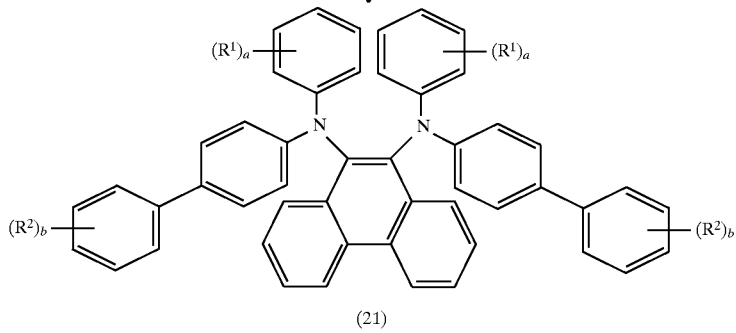

(21)

[wherein $R^1$, $R^2$, a and b are the same as described above].

Specifically, N,N'-diacetyl-9,10-phenanthrylenediamine and an iodobenzene derivative (10) in a molar ratio of 1:2 are mixed with copper, copper oxide or a copper halide, and allowed to react in the presence of a basic substance to give an intermediate reaction product (11). In turn, the intermediate reaction product (11) is allowed to react in a suitable solvent containing hydrochloric acid to give a deacetylated intermediate product (12), which is then allowed to react with a 4-iodobiphenyl derivative (13) in a molar ratio of 1:2 in the same manner as described above.

The aforesaid phenanthrylenediamine derivatives according to the present invention can be suitably used as an electric charge transferring material, particularly as a hole transferring material, in such applications as solar batteries, electroluminescent devices, electrophotosensitive materials and the like, and utilized in other various fields.

The electrophotosensitive material according to the present invention will hereinafter be described in detail.

The electrophotosensitive material of the present invention comprises a photosensitive layer provided on a conductive substrate and containing one or more phenanthrylenediamine derivatives represented by the general formula (1). The photosensitive layer may be of a so-called single-layer type or of a so-called multi-layer type in accordance with the present invention.

For formation of the single-layer photosensitive layer, a phenanthrylenediamine derivative represented by the general formula (1) as an electric charge transferring material, an electric charge generating material, a binding resin and the like are dissolved or dispersed in a suitable solvent, and then a coating liquid thus prepared is applied on the conductive substrate by a coating method or the like, and dried.

For formation of the multi-layer photosensitive layer, an electric charge generating layer containing an electric charge generating material is first formed on the conductive substrate by vapor deposition, application of a coating liquid containing the electric charge generating material and a binding resin, or a like method. Then, an electric charge transferring layer is formed by applying a coating liquid containing a phenanthrylenediamine derivative represented by the general formula (1) as an electric charge transferring material and a binding resin on the electric charge generating layer by a coating method or the like, and drying the coating liquid. To the contrary, the electric charge transferring layer may be first formed on the conductive substrate and then the electric charge generating layer may be formed thereon.

Examples of the electric charge generating material include, though not limited thereto, powdery inorganic photoconductive materials such as selenium, selenium-tellurium, selenium-arsenic, cadmium sulfide, α-silicon; anthanthrone pigments, triphenylmethane pigments, therene pigments, toluidine pigments, pyrazoline pigments, quinacridone pigments, and compounds represented by the general formulae (CG1) to (CG12):

(CG1) Metal-free phthalocyanine pigment (PcH$_2$)

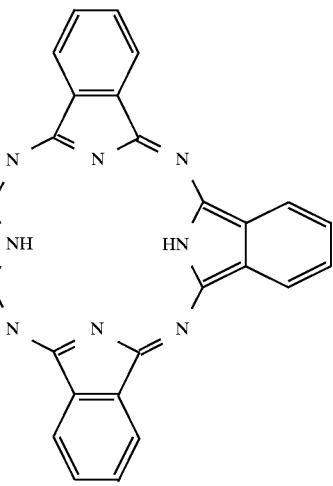

(CG1)

(CG2) Titanylphthalocyanine pigment (PcTiO)

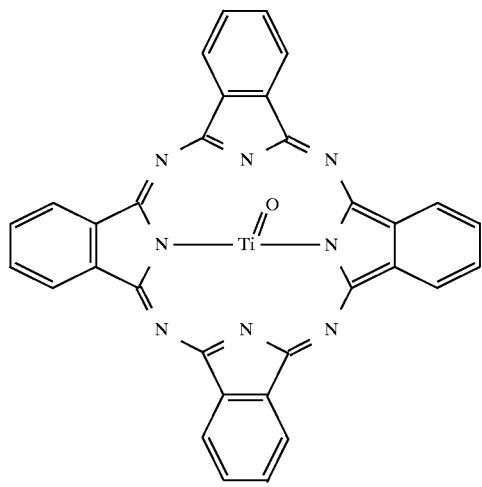

(CG2)

(CG3) Perylene pigment

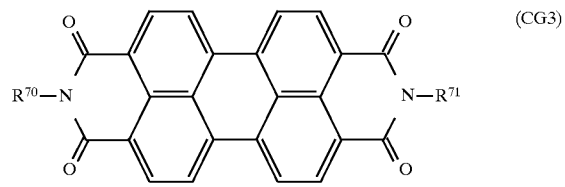

(CG3)

[wherein $R^{70}$ and $R^{71}$ are the same or different and each represents an alkyl group having not more than 18 carbons and optionally having a substituent, a cycloalkyl group, an aryl group, an alkanoyl group or an aralkyl group]

(CG4) Bis-azo pigment $$A^1-N=N-X-N=N-A^2 \quad (CG4)$$

[wherein $A^1$ and $A^2$ are the same or different and each represents a coupler residue; and X represents

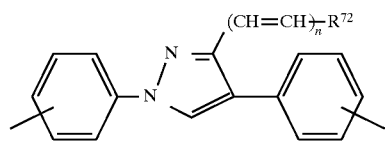

(wherein $R^{72}$ represents a hydrogen atom, a alkyl group optionally having a substituent, an aryl group optionally having a substituent, or a heterocyclic group; and n represents 0 or 1),

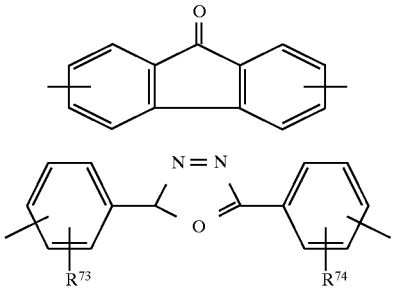

(wherein $R^{73}$ and $R^{74}$ are the same or different and each represents a hydrogen atom, an alkyl group having 1 to 5 carbons, a halogen atom, an alkoxy group, an aryl group or an aralkyl group),

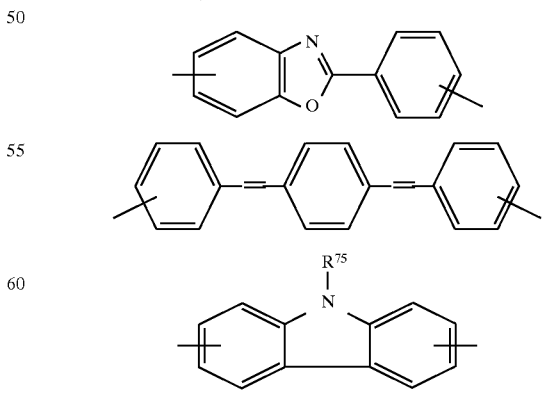

(wherein $R^{75}$ represents a hydrogen atom, an ethyl group, a chloroethyl group or a hydroxyethyl group),

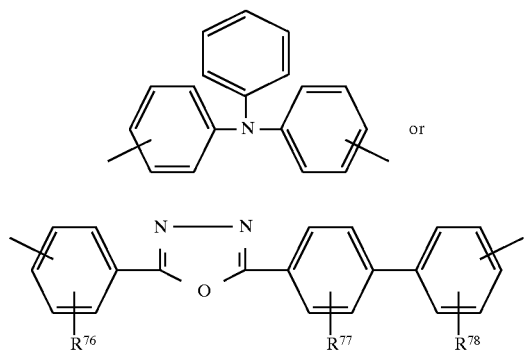

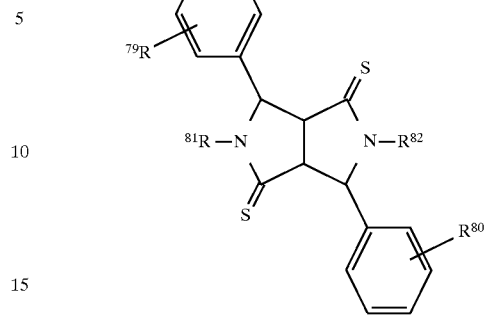

(CG5) Dithioketopyrrolopyrrole pigment (wherein $R^{76}$, $R^{77}$ and $R^{78}$ are the same or different and each represents a hydrogen atom, an alkyl group having 1 to 5 carbons, a halogen atom, an alkoxy group, an aryl group or an aralkyl group)]

[wherein $R^{79}$ and $R^{80}$ are the same or different and each represents a hydrogen atom, an alkyl group, an alkoxy group or a halogen atom; $R^{81}$ and $R^{82}$ are the same or different and each represents a hydrogen atom, an alkyl group or an aryl group]

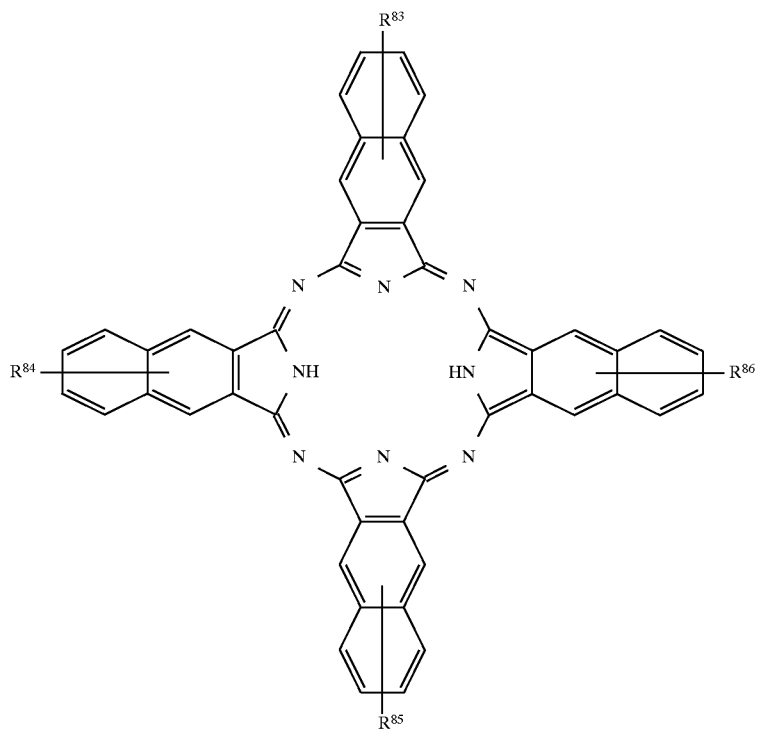

[wherein $R^{83}$ $R^{84}$ $R^{85}$ and $R^{86}$ are the same or different and each represents a hydrogen atom, an alkyl group, an alkoxy group or a halogen atom]

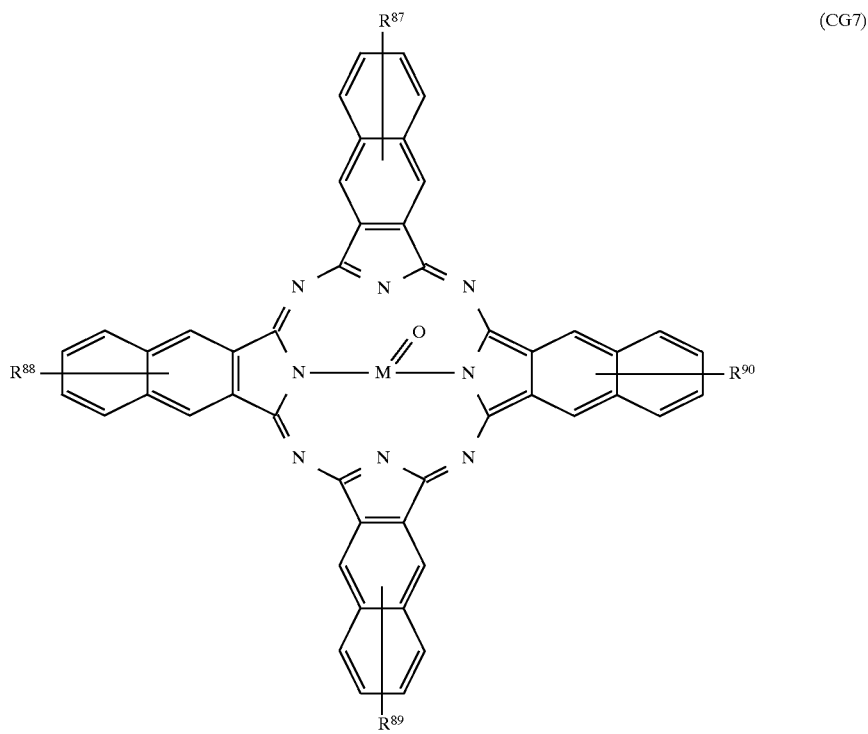

[wherein $R^{87}$, $R^{88}$, $R^{89}$ and $R^{90}$ are the same or different and each represents a hydrogen atom, an alkyl group, an alkoxy group or a halogen atom; and M represents Ti or V]

(CG8) Squaraine pigment

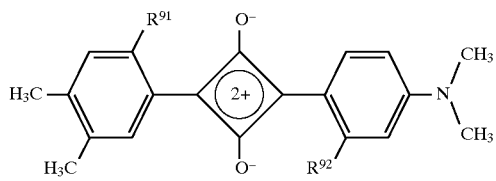

[wherein $R^{91}$ and $R^{92}$ are the same or different and each represents a hydrogen atom, an alkyl group, an alkoxy group or a halogen atom]

(CG9) tris-azo pigment

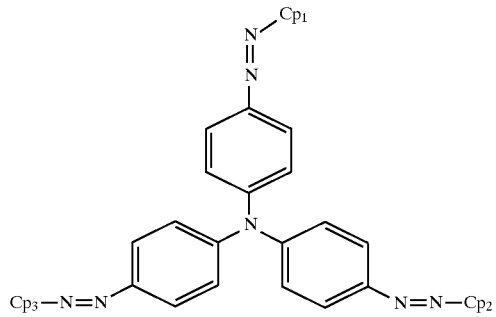

[wherein $Cp_1$, $CP_2$ and $Cp_3$ are the same or different and each represents a coupler residue]

(CG10) Indigo pigment

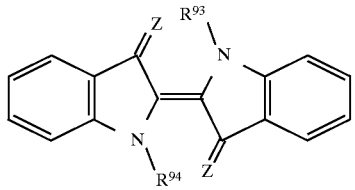

[wherein $R^{93}$ and $R^{94}$ are the same or different and each represents a hydrogen atom, an alkyl group or an aryl group; and Z represents an oxygen atom or a sulfur atom]

(CG11) Azulenium pigment

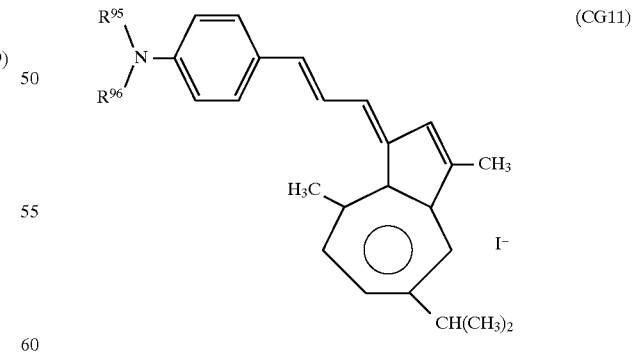

[wherein $R^{95}$ and $R^{96}$ are the same or different and each represents a hydrogen atom, an alkyl group or an aryl group]

(CG12) Cyanine pigment

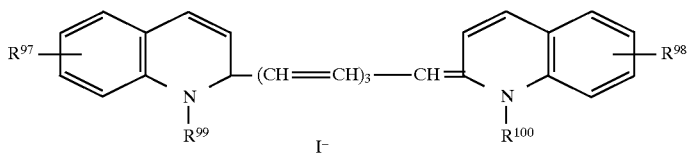

[wherein $R^{97}$ and $R^{98}$ are the same or different and each represents a hydrogen atom, an alkyl group, an alkoxy group or a halogen atom; and $R^{99}$ and $R^{100}$ are the same or different and each represents a hydrogen atom, an alkyl group or an aryl group]

In the aforesaid exemplary electric charge generating materials, examples of the alkyl groups include those as previously described. Examples of the alkyl groups having 1 to 5 carbons include the aforesaid exemplary alkyl groups having 1 to 6 carbons, except a hexyl group. Examples of the alkyl group having not more than 18 carbons and optionally having a substituent include, in addition to the aforesaid alkyl groups having 1 to 6 carbons, an octyl group, a nonyl group, a decyl group, a dodecyl group, a tridecyl group, a pentadecyl group, an octadecyl group and the like. Examples of the cycloalkyl group include those having 3 to 8 carbons such as a cyclopropyl group, a cyclobutyl group, a cyclopentyl group, a cyclohexyl group, a cycloheptyl group and a cyclooctyl group. Examples of the alkoxy groups and the aryl groups include those as previously described. Examples of the aralkyl groups include those having a 1- to 6-carbon alkyl group such as a benzyl group, a benzhydryl group, a trityl group and a phenethyl group. Examples of the alkanoyl group include a formyl group, an acetyl group, a propionyl group, a butyryl group, a pentanoyl group and a hexanoyl group. Examples of the heterocyclic group include a thienyl group, a pyrrolyl group, a pyrrolidinyl group, an oxazolyl group, an isoxazolyl group, a thiazolyl group, an isothiazolyl group, an imidazolyl group, a 2H-imidazolyl group, a pyrazolyl group, a triazolyl group, a tetrazolyl group, a pyranyl group, a pyridyl group, a piperidyl group, a piperidino group, a 3-morpholinyl group and a morpholino group. The heterocyclic group may be condensed with an aromatic ring.

Examples of the optional substituents include halogen atoms, an amino group, a hydroxyl group, a carboxyl group optionally esterified, a cyano group, alkyl groups having 1 to 6 carbons, alkoxy groups having 1 to 6 carbons, alkenyl groups having 2 to 6 carbons and optionally having an aryl group.

Examples of the coupler residues represented by $A^1$, $A^2$, $Cp_1$, $CP_2$ and $Cp_3$ include groups represented by the following general formulae (51) to (57).

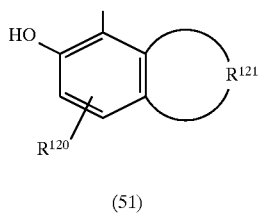

(51)

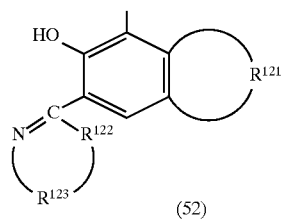

(52)

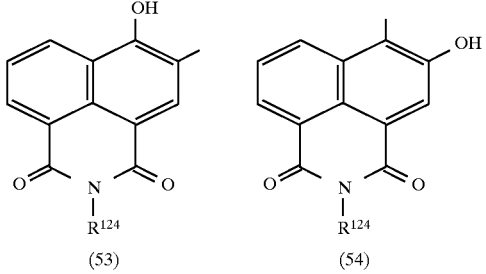

(53)         (54)

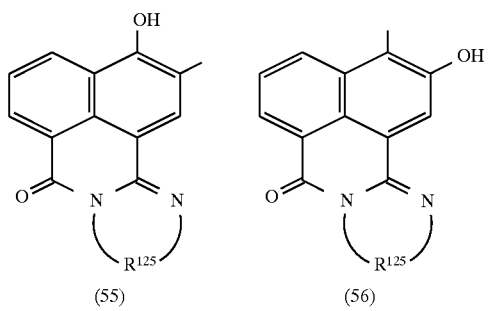

(55)         (56)

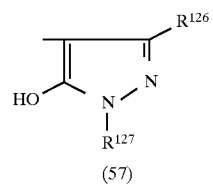

(57)

In the foregoing general formulae, $R^{120}$ represents a carbamoyl group, a sulfamoyl group, an allophanoyl group, an oxamoyl group, an anthraniloyl group, a carbazoyl group, a glycyl group, a hydantoyl group, a phthalamoyl group or a succinamoyl group. These groups may each have a substituent such as a halogen atom, a phenyl group optionally having a substituent, a naphthyl group optionally having a substituent, a nitro group, a cyano group, an alkyl group, an alkenyl group, a carbonyl group or a carboxyl group.

$R^{121}$ represents an atomic group which is required to form an aromatic ring, a polycyclic hydrocarbon or a heterocyclic ring by condensation with the benzene ring. These rings may each have any of the aforesaid substituents.

$R^{122}$ represents an oxygen atom, a sulfur atom or an imino group.

$R^{123}$ represents a divalent chain hydrocarbon group or an aromatic hydrocarbon group. These groups may each have any of the aforesaid substituents.

$R^{124}$ represents an alkyl group, an aralkyl group, an aryl group or a heterocyclic group. These groups may each have any of the aforesaid substituents.

$R^{125}$ represents a divalent chain hydrocarbon group, an aromatic hydrocarbon group or an atomic group-which is required to form a heterocyclic ring cooperatively with a portion of the aforesaid general formula (55) or (56) represented by the formula (58) and optionally has any of the aforesaid substituents.

 (58)

$R^{126}$ represents a hydrogen atom, an alkyl group, an amino group, a carbamoyl group, a sulfamoyl group, an allophanoyl group, a carboxyl group, an alkoxycarbonyl group, an aryl group or a cyano group. These groups except the hydrogen atom may each have any of the aforesaid substituents.

$R^{127}$ represents an alkyl group or an aryl group. These groups may each have any of the aforesaid substituents.

Examples of the alkenyl groups include those having 2 to 6 carbons such as a vinyl group, an allyl group, a 2-butenyl group, a 3-butenyl group, a 1-methylallyl group, a 2-pentenyl group and a 2-hexenyl group.

In the group $R^{121}$, examples of the atomic group required for the formation of the aromatic ring by the condensation with the benzene ring include alkylene groups such as a methylene group, an ethylene group, a propylene group and a butylene group.

Examples of the aromatic ring to be formed by the condensation of the group $R^{121}$ with the benzene ring include a naphthalene ring, an anthracene ring, a phenanthrene ring, a pyrene ring, a chrysene ring and a naphthacene ring.

In the group $R^{121}$, examples of the atomic group required for the formation of the polycyclic hydrocarbon by the condensation with the benzene ring include alkylene groups having 1 to 4 carbons such as a methylene group, an ethylene group, a propylene group and a butylene group.

In the group $R^{121}$, examples of the atomic group required for the formation of the polycyclic hydrocarbon by the condensation with the benzene ring further include a carbazole ring, benzocarbazole rings and a dibenzofuran ring.

In the group $R^{121}$, examples of the atomic group required for the formation of the heterocyclic ring by the condensation with the benzene ring include a benzofuranyl group, a benzothiophenyl group, an indolyl group, a 1H-indolyl group, a benzoxazolyl group, a benzothiazolyl group, a 1H-indadolyl group, a benzimidazolyl group, a chromenyl group, a chromanyl group, an isochromanyl group, a quinolinyl group, an isoquinolinyl group, a cinnolinyl group, a phthalazinyl group, a quinazolinyl group, a quinoxalinyl group, a dibenzofuranyl group, a carbazolyl group, a xanthenyl group, an acridinyl group, a phenanthridinyl group, a phenazinyl group, a phenoxazinyl group and a thianthrenyl group.

Examples of the aromatic heterocyclic group to be formed by the condensation of the group $R^{121}$ with the benzene ring include a thienyl group, a furyl group, a pyrrolyl group, a oxazolyl group, an isoxazolyl group, a thiazolyl group, an isothiazolyl group and an imidazolyl group, a pyrazolyl group, a triazolyl group, a tetrazolyl group and a pyridyl group. These groups may be condensed with another aromatic group to form heterocyclic groups (e.g., benzofuranyl group, benzimidazolyl group, a benzoxazolyl group, a benzothiazolyl group and a quinolyl group).

In the groups $R^{123}$ and $R^{125}$, examples of the divalent chain hydrocarbon include an ethylene group, a propylene group and a butylene group, and examples of the divalent aromatic hydrocarbon include a phenylene group, a naphthylene group and a phenanthrylene group.

In the group $R^{124}$, examples of the heterocyclic group include a pyridyl group, a pyrazyl group, a thienyl group, a pyranyl group and an indolyl group.

In the group $R^{125}$, examples of the atomic group required to form the heterocyclic ring cooperatively with the portion represented by the formula (58) include a phenylene group, a naphthylene group, a phenanthrylene group, an ethylene group, a propylene group and a butylene group.

Examples of the aromatic heterocyclic group to be defined by the group $R^{125}$ and the portion represented by the formula (58) include a benzimidazole group, a benzo[f]benzimidazole group, a dibenzo[e,g]benzimidazole group and a benzopyrimidine group. These groups may each have any of the aforesaid substituents.

In the group $R^{126}$, examples of the alkoxycarbonyl group include a methoxycarbonyl group, an ethoxycarbonyl group, a propoxycarbonyl group and a butoxycarbonyl group.

These electric charge generating materials may be used either alone or in combination in accordance with the sensitivity range of the electrophotosensitive material.

Exemplary electric charge generating materials suitable for an organic photosensitive material having a sensitivity wavelength range of 700 nm or greater include phthalocyanine pigments such as X-type metal-free phthalocyanine and oxotitanylphthalocyanine. An electrophotosensitive material employing any of these phthalocyanine pigments as the electric charge generating material and the phenanthrylenediamine derivative of the present invention represented by the general formula (1) as the electric charge transferring material is highly sensitive in the aforesaid wavelength range, and can be suitably used in image forming apparatuses with a digital optical system such as a laser beam printer and a facsimile machine.

Exemplary electric charge generating materials suitable for an organic photosensitive material which is highly sensitive in the visible range include azo pigments and perylene pigments. An electrophotosensitive material employing any of these pigments as the electric charge generating material and the phenanthrylenediamine derivative of the present invention represented by the general formula (1) as the electric charge transferring material is highly sensitive in the visible range, and can be suitably used in image forming apparatuses with an analog optical system such as an electrostatic copying machine.

The phenanthrylenediamine derivative represented by the general formula (1) can be used alone as the electric charge transferring material or, alternatively, may be used in combination with other electric charge transferring materials.

Such other electric charge transferring materials include various electron transferring materials and hole transferring materials. Examples of the electron transferring materials include compounds represented by the general formulae (ET1) to (ET14):

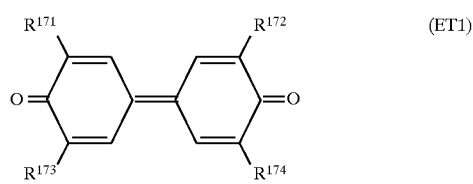 (ET1)

[wherein $R^{171}$, $R^{172}$ $R^{173}$ and $R^{174}$ are the same or different and each represents a hydrogen atom, an alkyl group optionally having a substituent, an alkoxy group optionally having a substituent, an aryl group optionally having a substituent, an aralkyl group optionally having a substituent, a cycloalkyl group optionally having a substituent, or a amino group optionally having a substituent; and two of the groups $R^{171}$, $R^{172}$ $R^{173}$ and $R^{174}$ are the same];

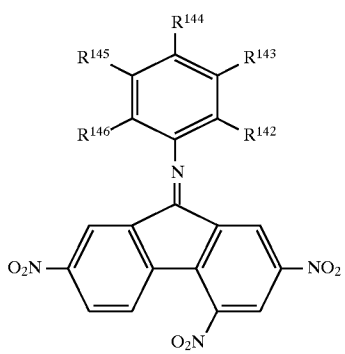

(ET2)

[wherein $R^{142}$, $R^{143}$ $R^{144}$, $R^{145}$ and $R^{146}$ are the same or different and each represents a hydrogen atom, an alkyl group optionally having a substituent, an alkoxy group optionally having a substituent, an aryl group optionally having a substituent, an aralkyl group optionally having a substituent, a phenoxy group optionally having a substituent, or a halogen atom];

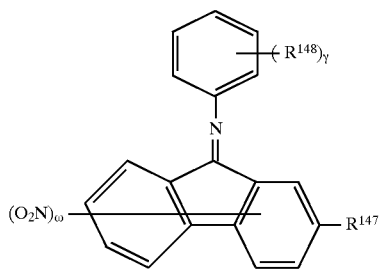

(ET3)

[wherein $R^{147}$ represents an alkyl group; $R^{148}$ represents an alkyl group optionally having a substituent, an alkoxy group optionally having a substituent, an aryl group optionally having a substituent, an aralkyl group optionally having a substituent, or a halogen atom; ω represents an integer from 0 to 4; γ represents an integer from 0 to 5; and if γ is 2 or greater, the groups $R^{148}$ may be different from each other];

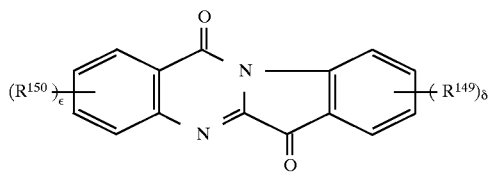

(ET4)

[wherein $R^{149}$ and $R^{150}$ are the same or different and each represents an alkyl group; δ represents an integer from 1 to 4; ε represents an integer from 0 to 4; and if δ or ε is 2 or greater, the groups $R^{149}$ or $R^{150}$ may be different from each other];

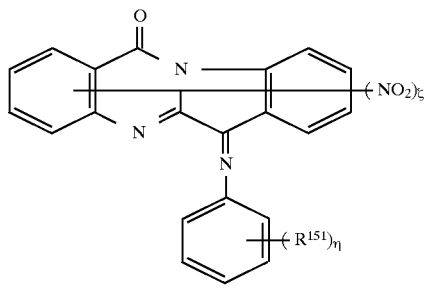

(ET5)

[wherein $R^{151}$ represents an alkyl group, an aryl group, an aralkyl group, an alkoxy group or a halogen atom; ζ represents an integer from 0 to 4; η represents an integer from 0 to 5; and if η is 2 or greater, the groups $R^{151}$ may be different from each other];

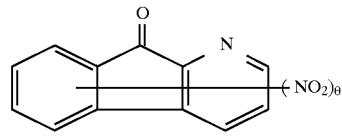

(ET6)

[wherein θ is an integer from 1 to 2];

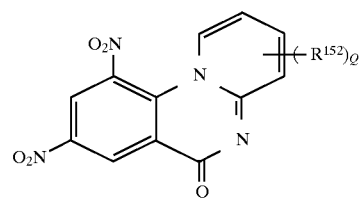

(ET7)

[wherein $R^{152}$ represents an alkyl group; σ represents an integer from 1 to 4; and if σ is 2 or greater, the groups $R^{152}$ may be different from each other];

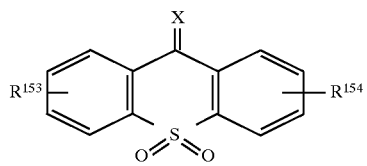

(ET8)

[wherein $R^{153}$ and $R^{154}$ are the same or different and each represents a hydrogen atom, a halogen atom, an alkyl group, an aryl group, aralkyloxycarbonyl group, an alkoxy group, a hydroxyl group, a nitro group or a cyano group; and X represents an oxygen atom, or a group of N—CN or C(CN)$_2$];

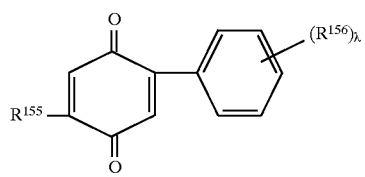

(ET9)

[wherein $R^{155}$ represents a halogen atom, an alkyl group or a phenyl group optionally having a substituent; $R^{156}$ represents a hydrogen atom, a halogen atom, an alkyl group optionally having a substituent, a phenyl group optionally having a substituent, an alkoxycarbonyl group, an N-alkylcarbamoyl group, a cyano group or a nitro group; λ represents an integer from 0 to 3; and if λ is 2 or greater, the groups $R^{156}$ may be different from each other];

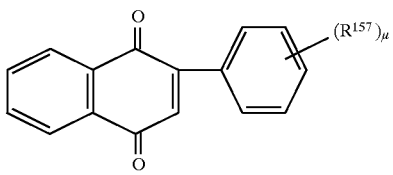

(ET10)

[wherein $R^{157}$ represents an alkyl group optionally having a substituent, a phenyl group optionally having a substituent, a halogen atom, an alkoxycarbonyl group, an N-alkylcarbamoyl group, a cyano group or a nitro group; μ represents an integer from 0 to 3; and if μ is 2 or greater, the groups $R^{157}$ may be different from each other];

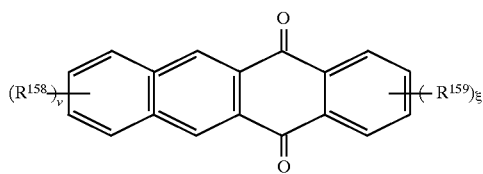
(ET11)

[wherein $R^{158}$ and $R^{159}$ are the same or different and each represents a halogen atom, an alkyl group optionally having a substituent, a cyano group, a nitro group or an alkoxycarbonyl group; ν and ξ each represent an integer from 0 to 3; and if ν or ξ is 2 or greater, the groups $R^{158}$ or $R^{159}$ may be different from each other];

(ET12)

[wherein $R^{160}$ and $R^{161}$ are the same or different and each represents a phenyl group, a polycyclic aromatic group or a heterocyclic group, which optionally has a substituent];

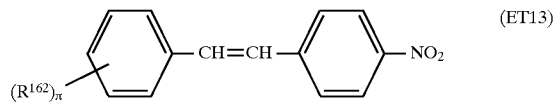
(ET13)

[wherein $R^{162}$ represents an amino group, a dialkylamino group, an alkoxy group, an alkyl group or a phenyl group; π represents an integer from 1 to 2; and if π is 2, the groups $R^{162}$ may be different from each other];

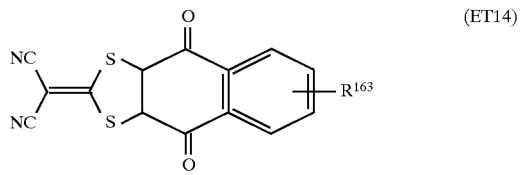
(ET14)

[wherein $R^{163}$ represents a hydrogen atom, an alkyl group, an aryl group, an alkoxy group or an aralkyl group].

Examples of the electron transferring material further include malononitrile, thiopyran compounds, tetracyanoethylene, 2,4,8-trinitrothioxanthone, dinitrobenzene, dinitroanthracene, dinitroacridine, nitroanthraquinone, dinitroanthraquinone, succinic anhydride, maleic anhydride and dibromomaleic anhydride.

In the aforesaid exemplary electron transferring materials, the examples of the alkyl groups, the alkoxy groups, the aryl groups, the aralkyl groups, the heterocyclic group and halogen atoms include those previously described. Examples of the polycyclic aromatic group include a naphthyl group, a phenanthryl group and an anthryl group. The examples of the optional substituents include those previously described.

Other exemplary electron transferring materials include electron attractive materials such as benzoquinone compounds, malononitrile, thiopyran compounds, tetracyanoethylene, tetracyanoquinodimethane, chloranil, bromanil, 2,4,7-trinitro-9-dicyanomethylenefluorenone, 2,4,5,7-tetranitroxanthone, 2,4,8-trinitrothioxanthone, dinitrobenzene, dinitroanthracene, dinitroacridine, nitroanthraquinone, dinitroanthraquinone, succinic anhydride, maleic anhydride and dibromomaleic anhydride, and polymeric materials obtained by polymerization of any of these electron attractive materials.

Examples of the hole transferring material include compounds represented by the general formula (HT1) to (HT12):

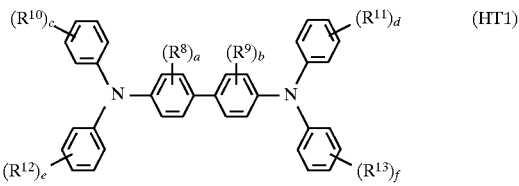
(HT1)

[wherein $R^8$, $R^9$, $R^{10}$, $R^{11}$, $R^{12}$ and $R^{13}$ are the same or different and each represents a halogen atom, an alkyl group optionally having a substituent, an alkoxy group optionally having a substituent, or an aryl group optionally having a substituent; a and b are the same or different and each represents an integer from 0 to 4; c, d, e and f are the same or different and each represents an integer from 0 to 5; and if a, b, c, d, e or f is 2 or greater, the groups $R^8$, $R^9$, $R^{10}$, $R^{11}$, $R^{12}$ or $R^{13}$ may be different from each other];

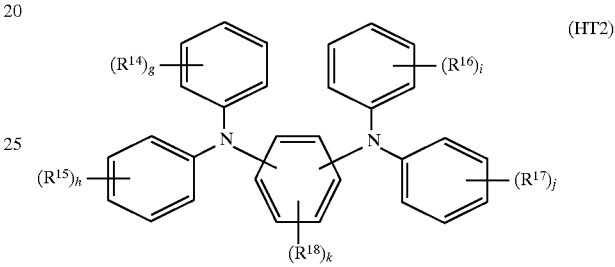
(HT2)

[wherein $R^{14}$, $R^{15}$, $R^{16}$, $R^{17}$ and $R^{18}$ are the same or different and each represents a halogen atom, an alkyl group optionally having a substituent, an alkoxy group optionally having a substituent, or an aryl group optionally having a substituent; g, h, i and j are the same or different and each represents an integer from 0 to 5; k represents an integer from 0 to 4; and if g, h, i, j or k is 2 or greater, the groups $R^{14}$, $R^{15}$, $R^{16}$, $R^{17}$ or $R^{18}$ may be different from each other];

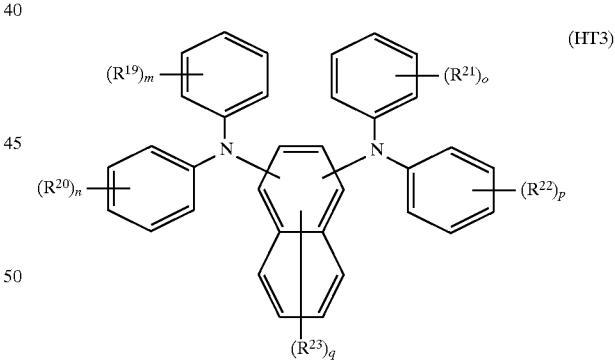
(HT3)

[wherein $R^{19}$, $R^{20}$, $R^{21}$ and $R^{22}$ are the same or different and each represents a halogen atom, an alkyl group optionally having a substituent, an alkoxy group optionally having a substituent, or an aryl group optionally having a substituent; $R^{23}$ represents a hydrogen atom, a halogen atom, a cyano group, a nitro group, an alkyl group optionally having a substituent, an alkoxy group optionally having a substituent, or an aryl group optionally having a substituent; m, n, o and p are the same or different and each represents an integer from 0 to 5; q represents an integer from 0 to 6; and if m, n, o, p or q is 2 or greater, the groups $R^{19}$, $R^{20}$, $R^{21}$, $R^{22}$ or $R^{23}$ may be different from each other];

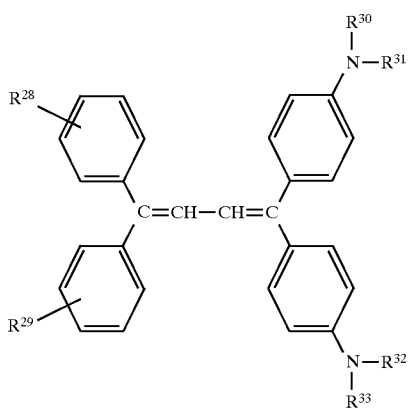

(HT4)

[wherein $R^{28}$ and $R^{29}$ are the same or different and each represents a hydrogen atom, a halogen atom, an alkyl group or an alkoxy group; and $R^{30}$, $R^{32}$ and $R^{33}$ are the same or different and each represents a hydrogen atom, an alkyl group or an aryl group];

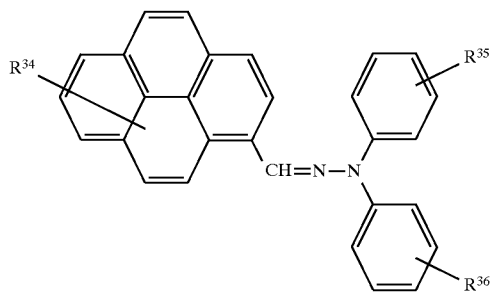

(HT5)

[wherein $R^{34}$, $R^{35}$ and $R^{36}$ are the same or different and each represents a hydrogen atom, a halogen atom, an alkyl group or an alkoxy group];

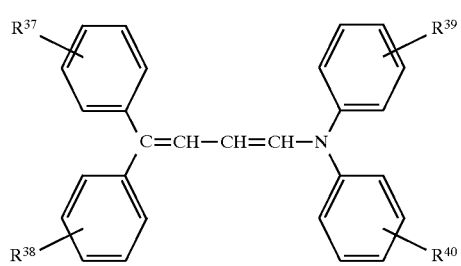

(HT6)

[wherein $R^{37}$, $R^{38}$, $R^{39}$ and $R^{40}$ are the same or different and each represents a hydrogen atom, a halogen atom, an alkyl group or an alkoxy group];

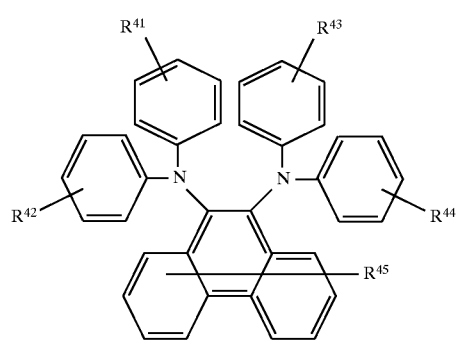

(HT7)

[wherein $R^{41}$, $R^{42}$, $R^{43}$, $R^{44}$ and $R^{45}$ are the same or different and each represents a hydrogen atom, a halogen atom, an alkyl group or an alkoxy group];

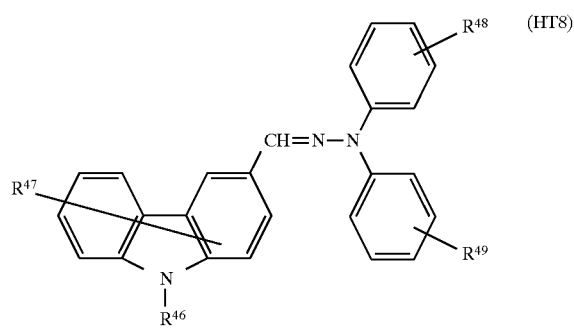

(HT8)

[wherein $R^{46}$ represents a hydrogen atom or an alkyl group; $R^{47}$, $R^{48}$ and $R^{49}$ are the same or different and each represents a hydrogen atom, a halogen atom, an alkyl group or an alkoxy group];

(HT9)

[wherein $R^{50}$, $R^{51}$ and $R^{52}$ are the same or different and each represents a hydrogen atom, a halogen atom an alkyl group or an alkoxy group];

(HT10)

[wherein $R^{53}$ and $R^{54}$ are the same or different and each represents a hydrogen atom, a halogen atom, an alkyl group optionally having a substituent, or an alkoxy group optionally having a substituent; $R^{55}$ and $R^{56}$ are the same or different and each represents a hydrogen atom, an alkyl group optionally having a substituent, or an aryl group optionally having a substituent];

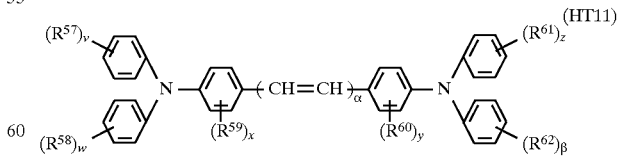

(HT11)

[wherein $R^{57}$, $R^{58}$, $R^{59}$, $R^{60}$, $R^{61}$ and $R^{62}$ are the same or different and each represents an alkyl group optionally having a substituent, an alkoxy group optionally having a substituent, or an aryl group optionally having a substituent; $\alpha$ represents an integer from 1 to 10; v, w, x, y, z and $\beta$ are the same or different and each represents 0 to 2; and if v, w, x, y, z or β is 2, the groups $R^{57}$, $R^{58}$, $R^{59}$, $R^{60}$, $R^{61}$ or $R^{62}$ may be different from each other];

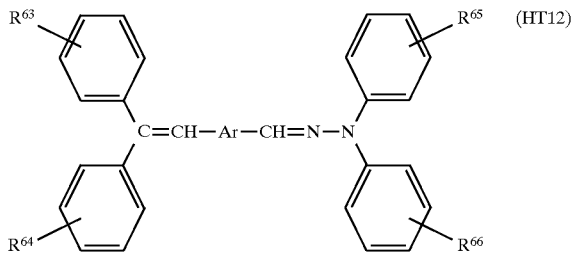

[wherein $R^{63}$, $R^{64}$, $R^{65}$ and $R^{66}$ are the same or different and each represents a hydrogen atom, a halogen atom, an alkyl group or an alkoxy group; and Ar represents the following group Ar1, Ar2 or Ar3].

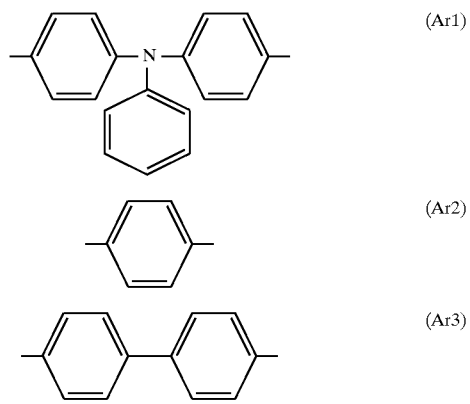

In the aforesaid exemplary hole transferring materials, examples of the alkyl groups include those previously described. Examples of the alkoxy groups include those having 1 to 6 carbons such as a methoxy group, an ethoxy group, a n-propoxy group, an isopropoxy group, a n-butoxy group, an isobutoxy group, a s-butoxy group, a t-butoxy group, a pentyloxy group and a hexyloxy group. Examples of the aryl groups include a phenyl group, a tolyl group, a xylyl group, a biphenyl group, an o-terphenyl group, a naphthyl group, an anthryl group and a phenanthryl group. Examples of the halogen atoms include a fluorine atom, a chlorine atom, a bromine atom and an iodine atom.

Examples of the optional substituents include halogen atoms, an amino group, a hydroxyl group, a carboxyl group optionally esterified, a cyano group, alkyl groups having 1 to 6 carbons, alkoxy groups having 1 to 6 carbons, and alkenyl groups having 2 to 6 carbons and optionally having an aryl group. The positions for substitution are not particularly limited.

Other exemplary hole transferring materials include electron donative materials such as condensed polycyclic compounds and nitrogen-containing cyclic compounds, e.g., diazole compounds such as 2,5-di(4-methylaminophenyl)-1,3,4-oxadiazole, styryl compounds such as 9-(4-diethylaminostyryl) anthracene, carbazole compounds such as polyvinyl carbazole, pyrazoline compounds such as 1-phenyl-3-(p-dimethylaminophenyl)pyrazoline, hydrazone compounds, triphenylamine compounds, indole compounds, oxazole compounds, isoxazole compounds, thiazole compounds, thiadiazole compounds, imidazole compounds, pyrazole compounds and triazole compounds.

These electric charge transferring materials may be used either alone or in combination. Where an electric charge transferring material having a film-forming property such as polyvinyl carbazole, the binding resin is not necessarily required.

Examples of the binding resin to be used together with the electric charge generating material or the electric charge transferring material include thermoplastic resins such as styrene polymer, styrene-butadiene copolymer, styrene-acrylonitrile copolymer, styrene-maleic acid copolymer, acrylic polymer, styrene-acrylic copolymer, polyethylene, ethylene-vinyl acetate copolymer, chlorinated polyethylene, polyvinyl chloride, polypropylene, vinyl chloride-vinyl acetate copolymer, polyester, alkyd resin, polyamide, polyurethane, polycarbonate, polyallylate, polysulfone, diallyl phthalate resin, ketone resin, polyvinyl butyral resin and polyether resin; crosslinking thermosetting resins such as silicone resin, epoxy resin, phenol resin, urea resin and melamine resin; and photosetting resins such as epoxy-acrylate and urethane-acrylate. These binding resins may be used either alone or in combination.

The photosensitive layer may contain any of various additives such a sensitizer, a fluorene compound, an ultraviolet absorber, a plasticizer, a surfactant and a leveling agent in addition to the aforesaid respective components. To improve the sensitivity of the photosensitive material, a sensitizer such as terphenyl, halonaphthoquinone or acenaphthylene may be used in combination with the electric charge generating material.

For the multi-layer photosensitive material, the electric charge generating material and the binder resin constituting the electric charge generating layer may be used in various proportions, but it is preferred that 5 to 1,000 parts by weight, particularly 30 to 500 parts by weight, of the electric charge generating material is used with respect to 100 parts by weight of the binding resin.

The electric charge transferring material and the binding resin constituting the electric charge transferring layer may be used in various proportions within such a range as not to prevent the transportation of electric charge and as to prevent the crystallization. It is preferred that 10 to 500 parts by weight, particularly 25 to 200 parts by weight, of the electric charge transferring material containing the phenanthrylenediamine derivative represented by the general formula (1) is used with respect to 100 parts by weigh of the binding resin to facilitate the transportation of electric charge generated in the electric charge generating layer under light irradiation. Where the phenanthrylenediamine derivative represented by the general formula (1) is used alone as the electric charge transferring material, the aforesaid proportion of the electric charge transferring material means the content of the phenanthrylenediamine derivative.

The thickness of the multi-layer photosensitive layer is preferably such that the electric charge generating layer is formed in a thickness of about 0.01 to 5 μm, particularly about 0.1 to 3 μm, and the electric charge transferring layer is formed in a thickness of about 2 to 100 μm, particularly about 5 to 50 μm.

For the single-layer photosensitive material, it is preferred that 0.1 to 50 parts by weight, particularly 0.5 to 30 parts by weight, of the electric charge generating material and 20 to 500 parts by weight, particularly 30 to 200 parts by weight, of the electric charge transferring material containing the phenanthrylenediamine derivative represented by the general formula (1) are used with respect to 100 parts by weight of the binding resin. Where the phenanthrylenediamine derivative represented by the general formula (1) is used alone as the electric charge transferring material, the aforesaid proportion of the electric charge transferring material means the content of the phenanthrylenediamine derivative.

The single-layer photosensitive layer is preferably formed in a thickness of about 5 to 100 μm, particularly about about 10 to 50 μm.

A barrier layer may be formed between the conductive substrate and the photosensitive layer in the single-layer photosensitive material, or between the conductive substrate and the electric charge generating layer, between the conductive substrate and the electric charge transferring layer or between the electric charge generating layer and the electric charge transferring layer in the multi-layer photosensitive material, as long as the characteristics of the photosensitive material are not deteriorated. Further, a protective layer may be formed on the surface of the photosensitive material.

Various conductive materials can be used as a material for the conductive substrate to be formed with the aforesaid respective layers thereon. Examples thereof include metals such as aluminum, copper, tin, platinum, silver, iron, vanadium, molybdenum, chromium, cadmium, titanium, nickel, palladium, indium, stainless steel and brass; plastic materials vapor-deposited or laminated with the aforesaid metals; and glass materials coated with aluminum iodide, tin oxide, indium oxide and the like.

The conductive substrate may be made in a sheet form or a drum form in accordance with the construction of an image forming apparatus to be used therewith. The substrate itself may be conductive or, alternatively, only the surface of the substrate may be conductive. The conductive substrate preferably has a sufficient mechanical strength when used.

When the aforesaid respective layers are to be formed by a coating method, the electric charge generating material, the electric charge transferring material, the binding resin and the like respectively selected from the aforesaid examples may be mixed and dispersed in a suitable solvent by a known method, for example, using a roll mill, a ball mill, an atriter, a paint shaker, a supersonic dispenser or the like to prepare a coating liquid, which is applied by a known means and then dried.

Usable as the solvent for the preparation of the coating liquid are various organic solvents. Examples thereof include alcohols such as methanol, ethanol, isopropanol and butanol; aliphatic hydrocarbons such as n-hexane, octane and cyclohexane; aromatic hydrocarbons such as benzene, toluene and xylene; halogenated hydrocarbons such as dichloromethane, dichloroethane, carbon tetrachloride and chlorobenzene; ethers such as dimethyl ether, diethyl ether, tetrahydrofuran, ethylene glycol dimethyl ether and diethylene glycol dimethyl ether; ketones such as acetone, methyl ethyl ketone and cyclohexanone; esters such as ethyl acetate and methyl acetate; and dimethylformaldehyde, dimethylformamide and dimethylsulfoxide. These solvents may be used either alone or in combination.

A surfactant, a leveling agent and the like may be added to the coating liquid to improve the dispersibility of the electric charge transferring material and electric charge generating material as well as the smoothness of the surface of the photosensitive layer.

As described above, the phenanthrylenediamine derivative of the present invention has a high electric charge transferring capability and is excellent in the compatibility with a binding resin and the stability. Accordingly, the phenanthrylenediamine derivative can be suitably used as an electric charge transferring material, particularly as a hole transferring material, in such applications as solar batteries, electroluminescent devices, electrophotosensitive materials and the like.

Further, the electrophotosensitive material of the present invention, which comprises a photosensitive layer containing the aforesaid phenanthrylenediamine derivative as the electric charge transferring material, is superior in the sensitivity characteristics and the durability to the conventional electrophotosensitive materials, thereby contributing to improvements in the performance and operating speed of various image forming apparatuses such as electrostatic copying machine and laser beam printer.

EXAMPLES

The present invention will hereinafter be described by way of Synthesis Examples, Examples and Comparative Examples.

Synthesis of phenanthrylenediamine derivatives

Synthesis Example 1

Synthesis of N,N'-bis(4-biphenylyl)-N,N'-diphenyl-9,10-phenanthrylenediamine

First, 29.2 g of N,N'-diacetyl-9,10-phenanthrylenediamine, 40.8 g of iodobenzene, 27.6 g of potassium carbonate and 2 g of copper powder were added in 300 ml of nitrobenzene, and the mixture was refluxed in a nitrogen atmosphere under vigorous stirring for 24 hours. Water produced during the reaction was removed out of the reaction system by azeotropic distillation with nitrobenzene.

After the reaction solution was cooled, the inorganic substances were filtered off, and then nitrobenzene was distilled away by steam distillation. The obtained residue was added in 200 ml of tetrahydrofuran together with 50 ml of 10% hydrochloric acid. The mixture was deacetylated by refluxing for 2 hours to give N,N'-diphenyl-9,10-phenanthrylenediamine.

In turn, 18.0 g of the compound thus obtained, 27.9 g of 4-iodobiphenyl, 27.6 g of potassium carbonate and 2 g of copper powder were added in 300 ml of nitrobenzene, and the mixture was refluxed in a nitrogen atmosphere under vigorous stirring for 24 hours. Water produced during the reaction was removed out of the reaction system by azeotropic distillation with nitrobenzene.

After the reaction solution was cooled, the inorganic substances were filtered off, and then nitrobenzene was distilled away by steam distillation. The obtained residue was dissolved in cyclohexane, and purified by way of silica gel column chromatography. In turn, cyclohexane was distilled away to give a white precipitate, which was recrystallized from n-hexane to give the objective compound represented by the formula (2-1) (14.3 g, yield: 21.1%).

The results of the elemental analysis of the compound are shown below.

Elemental analysis (%) Calculated C: 88.70 H: 7.15 N: 4.14 Found C: 88.61 H: 7.19 N: 4.02

Synthesis Example 2

Synthesis of N,N'-bis[4-(4'-isopropyl)biphenylyl]-N,N'-di(4-methylphenyl)-9 10-phenanthrylenediamine The objective compound represented by the formula (2-3) (15.5 g, yield: 20.1%) was obtained in substantially the same manner as in Synthesis Example 1, except that 43.5 g of 4-iodotoluene was used instead of iodobenzene and 32.2 g of 4-isopropyl-4'-iodobiphenyl was used instead of 4-iodobiphenyl.

Elemental analysis (%) Calculated C: 89.60 H: 6.75 N: 3.61 Found C: 89.55 H: 6.79 N: 3.59

Synthesis Example 3

Synthesis of N,N'-bis[4-(4'-ethyl)biphenylyl]-N,N'-di(4-methylphenyl)-9,10-phenanthrylenediamine The objective compound represented by the formula (2-5) (13.6 g, yield: 18.2%) was obtained in substantially the same manner as in Synthesis Example 1, except that 4-iodotoluene was used instead of iodobenzene and 4-ethyl-4'-iodobiphenyl was used instead of 4-iodobiphenyl.

Elemental analysis (%) Calculated C: 89.79 H: 6.46 N: 3.74 Found C: 89.80 H: 6.39 N: 3.77

Synthesis Example 4

Synthesis of N,N,N',N'-tetrakis(4-biphenylyl)-9,10-phenanthrylenediamine

First, 20.8 g of 9,10-phenanthrylenediamine, 112.0 g of 4-iodobiphenyl, 27.6 g of potassium carbonate and 2 g of copper powder were added in 300 ml of nitrobenzene, and the mixture was refluxed in a nitrogen atmosphere under vigorous stirring for 24 hours. Water produced during the reaction was removed out of the reaction system by azeotropic distillation with nitrobenzene.

After the reaction solution was cooled, the inorganic substances were filtered off, and then nitrobenzene was distilled away by steam distillation. The obtained residue was dissolved in cyclohexane, and purified by way of silica gel column chromatography. In turn, cyclohexane was distilled away to give a white precipitate, which was recrystallized from n-hexane to give the objective compound represented by the formula (3-1) (23.9 g, yield: 29.2%).

Elemental analysis (%) Calculated C: 91.14 H: 5.43 N: 3.43 Found C: 91.20 H: 5.49 N: 3.31

Synthesis Example 5

Synthesis of N,N,N',N'-tetrakis(4'-ethylbiphenyl-4-yl)-9,10-phenanthrylenediamine The objective compound represented by the formula (3-3) (25.4 g, yield: 27.3%) was obtained in substantially the same manner as in Synthesis Example 4, except that 123.3 g of 4-ethyl-4'-iodobiphenyl was used instead of 4-iodobiphenyl.

Elemental analysis (%) Calculated C: 90.47 H: 6.51 N: 3.01 Found C: 90.42 H: 6.46 N: 3.11

Synthesis Example 6

Synthesis of N,N,N',N'-tetrakis(4'-methoxybiphenyl-4-yl)-9,10-phenanthrylenediamine The objective compound represented by the formula (3-5) (23.5 g, yield: 25.1%) was obtained in substantially the same manner as in Synthesis Example 4, except that 124.0 g of 4-methoxy-4'-iodobiphenyl was used instead of 4-iodobiphenyl.

Elemental analysis (%) Calculated C: 84.57 H: 5.60 N: 2.99 Found C: 84.47 H: 5.63 N: 3.06

Production of electrophotosensitive materials

Examples 1 to 3 and Comparative Examples 1 and 2 (Single-layer photosensitive materials for digital light source)

First, 5 parts by weight of an electric charge generating material (X-type metal-free phthalocyanine represented by the formula (CG1)), 100 parts by weight of an electric charge transferring material and 100 parts by weight of a binding resin (polycarbonate) were mixed and dispersed in 800 parts by weight of a solvent (tetrahydrofuran) by means of a ball mill for 50 hours to prepare a coating liquid for single-layer photosensitive layer. In turn, the coating liquid was applied on an aluminum tube serving as a conductive substrate by a dip coating method, and then dried in hot air at 110° C. for 30 minutes. Thus, single-layer photosensitive materials for digital light source according to Examples 1 to 3 and Comparative Examples 1 and 2 were produced which each had a 25 μm-thick single-layer photosensitive layer.

Used as the electric charge materials in Examples 1 to 3 were the phenanthrylenediamine derivatives of the present invention, which are shown in Table 1.

An m-phenylenediamine derivative (HT2-1) and a phenanthrylenediamine derivative (4-1) shown below were used as the electric charge transferring materials in Comparative Examples 1 and 2, respectively.

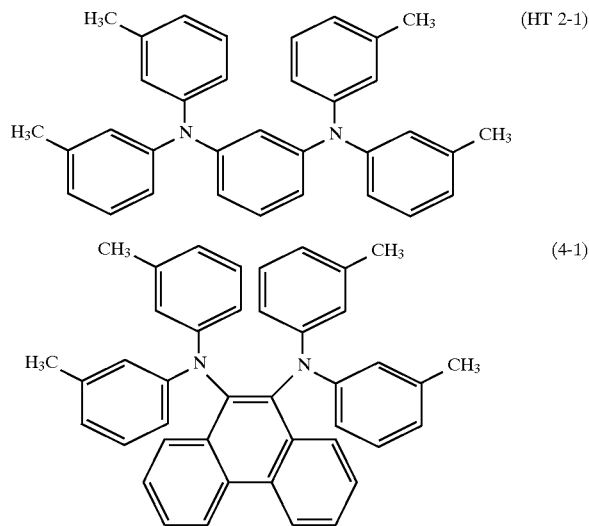

The characteristics of the thus produced electrophotosensitive materials of Examples 1 to 3 and Comparative Examples 1 and 2 were evaluated by performing a test (I) of initial electric characteristics and a test (I) of electric characteristics after repeated light exposure, as follows.

Test (I) of initial electric characteristics

By means of a drum sensitivity tester available from GENTEC CO., a surface potential $V_o$ (V) of each of the electrophotosensitive materials of Examples 1 to 3 and Comparative Examples 1 and 2 was measured when a voltage was applied on the surface thereof to charge the surface at +700±20V. Then, monochromatic light having a wavelength of 780 nm (half-width: 20 nm) and a light intensity of 10 μJ/cm$^2$ was extracted from white light of a halogen lamp (serving as an exposure light source) through a band-pass filter, and irradiated on the surface of the photosensitive material (irradiation time: 1.5 seconds). A time required for the surface potential to be reduced to half was measured, and a half-life exposure $E_{1/2}$ (μJ/cm$^2$) was calculated. A surface potential after a lapse of 0.5 second from the beginning of the light exposure was measured as a residual potential $V_r$ (V).

Test (I) of electric characteristics after repeated light exposure

After an image forming operation was performed 10,000 times by using each of the electrophotosensitive materials of Examples 1 to 3 and Comparative Examples 1 and 2 in a laser beam printer (Model TC-650 available from MITA INDUSTRIAL CO., LTD.), a surface potential $V_o$ (V) and a residual potential $V_r$ (V) were measured in the same manner as described above by means of the aforesaid drum sensitivity tester, and differences $\Delta V_o$ (V) and $\Delta V_r$ (V) between the measured values and the initial values were calculated.

The results are shown in Table 1.

TABLE 1

| | Electric charge generating material | Electric charge transferring material | Initial electric characteristics | | | After repeated light exposure | |
|---|---|---|---|---|---|---|---|
| | | | $V_o$ | $V_r$ | $E_{1/2}$ | $\Delta V_o$ | $\Delta V_r$ |
| Ex. 1 | CG1 | 3-1 | 700 | 50 | 1.37 | −20 | +5 |
| Ex. 2 | CG1 | 3-3 | 699 | 49 | 1.39 | −20 | +6 |
| Ex. 3 | CG1 | 3-5 | 700 | 50 | 1.35 | −15 | +7 |
| Com. Ex. 1 | CG1 | HT2-1 | 700 | 130 | 2.45 | −220 | +55 |
| Com. Ex. 2 | CG1 | 4-1 | 700 | 85 | 1.85 | −85 | +45 |

Examples 4 to 27 and Comparative Examples 3 to 16 (Single-layer photosensitive materials for analog light source)

Single-layer photosensitive materials for analog light source were each produced in substantially the same manner as in Examples 1 to 3 and Comparative Examples 1, except that 5 parts by weight of a perylene pigment represented by the formula (CG3-1) or each of bis-azo pigments represented by the formulae (CG4-1) to (CG4-7) was used as the electric charge generating material.

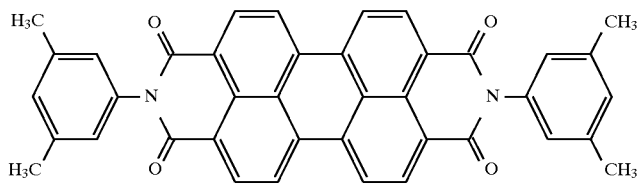

(CG 3-1)

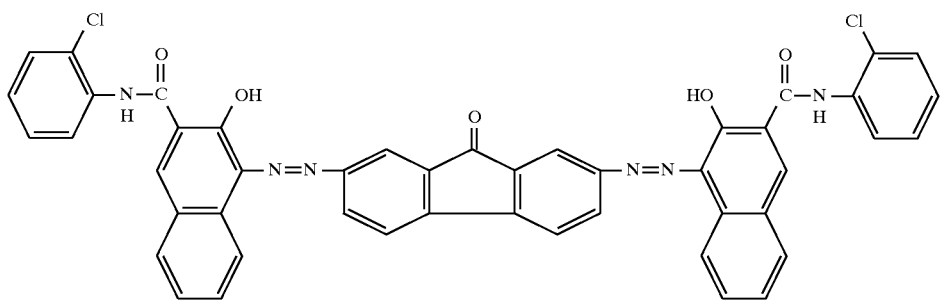

(CG 4-1)

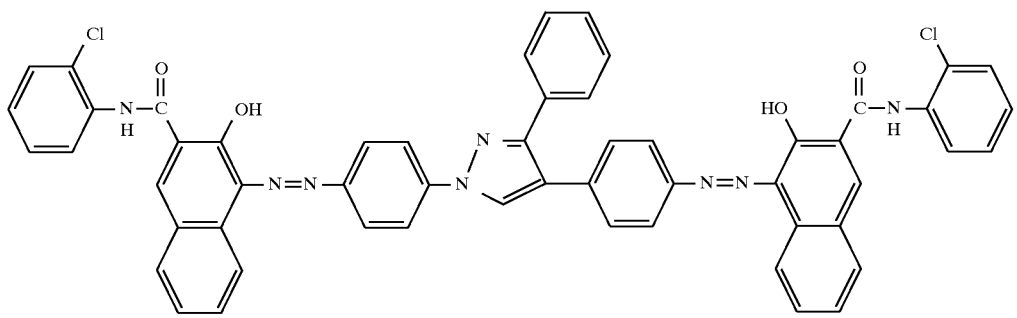

(CG 4-2)

-continued
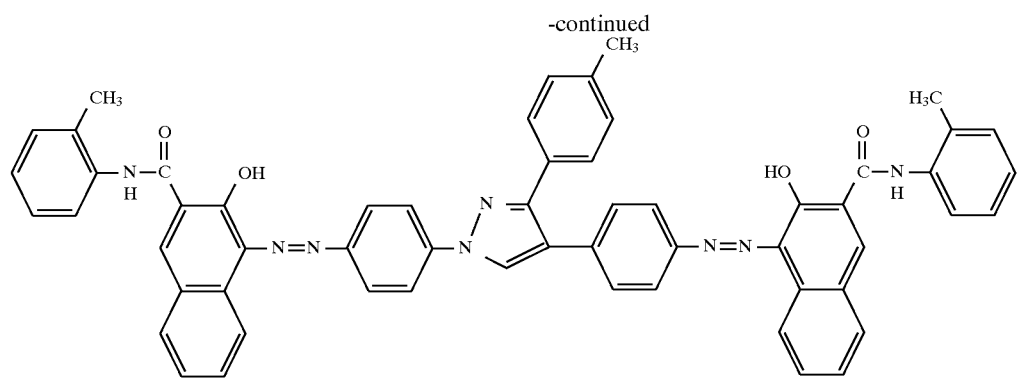
(CG 4-3)
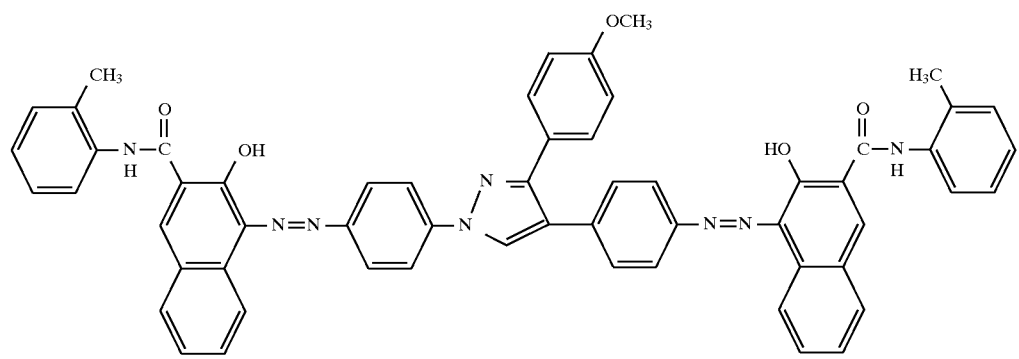
(CG 4-4)
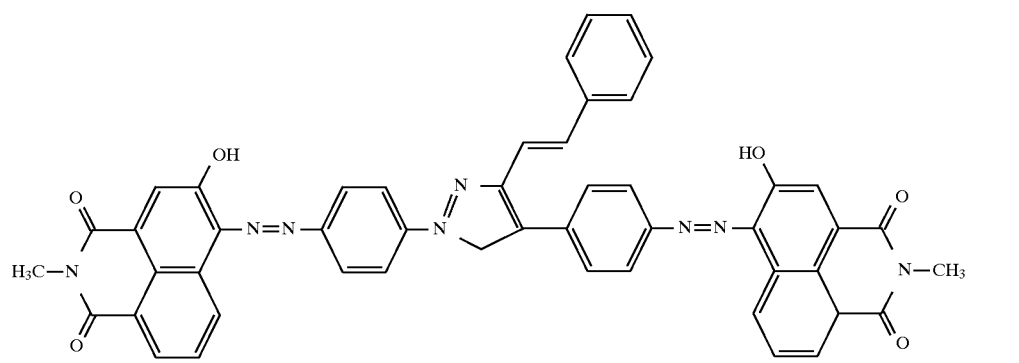
(CG 4-5)
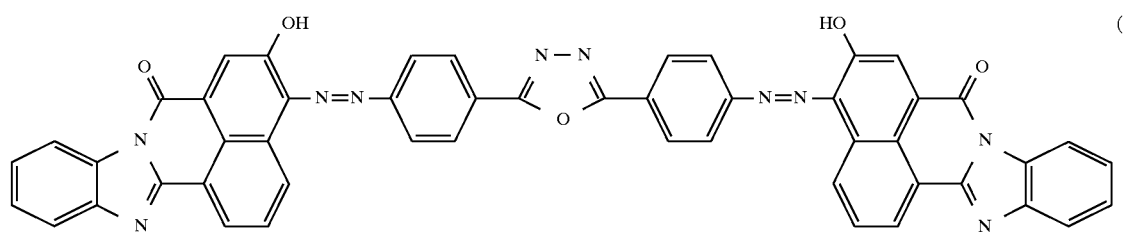
(CG 4-6)
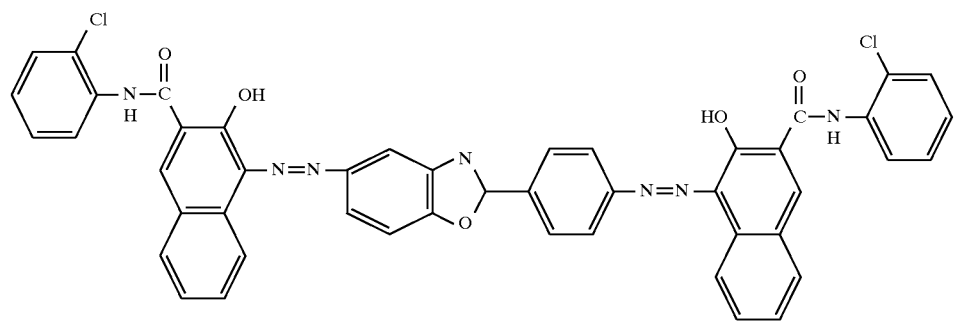
(CG 4-7)

The electric charge generating materials and electric charge transferring materials used in Examples 4 to 27 and Comparative Examples 3 to 16 are shown in Tables 2 and 3.

The characteristics of the thus produced electrophotosensitive materials of Examples 4 to 27 and Comparative Examples 3 to 16 were evaluated by performing a test (II) of initial electric characteristics and a test (II) of electric characteristics after repeated light exposure, as follows.

Test (II) of initial electric characteristics

Surface potentials $V_o$ (V) of the electrophotosensitive materials of Examples 4 to 27 and Comparative Examples 3 to 16 were each measured in the same manner as in the test (I) of initial electric characteristics. Then, white light (light intensity: 10 Lux) of a halogen lamp serving as an exposure light source was irradiated on the surface of each of the electrophotosensitive materials (irradiation time: 1.5 seconds). A half-life exposure $E_{1/2}$ (Lux-sec) was calculated and a residual potential $V_r$ (V) was measured in the same manner in the test (I) of initial electric characteristics.

Test (IT) of electric characteristics after repeated light

An image forming operation was performed 10,000 times by using each of the electrophotosensitive materials of Examples 4 to 27 and Comparative Examples 3 to 16 in an electrostatic copying machine (Model DC2556 available from MITA INDUSTRIAL CO., LTD.). Differences $\Delta V_o$ (V) and $\Delta V_r$ (V) were obtained in the same manner as in the test (I) of electric characteristics after repeated light exposure.

The results are shown in Tables 2 and 3.

TABLE 2

| | Electric charge generating material | Electric charge transferring material | Initial electric characteristics | | | After repeated light exposure | |
|---|---|---|---|---|---|---|---|
| | | | $V_o$ | $V_r$ | $E_{1/2}$ | $\Delta V_o$ | $\Delta V_r$ |
| Ex. 4 | CG3-1 | 3-1 | 700 | 137 | 1.85 | −60 | +15 |
| Ex. 5 | CG3-1 | 3-3 | 699 | 138 | 1.83 | −35 | +15 |
| Ex. 6 | CG3-1 | 3-5 | 698 | 130 | 1.85 | −20 | +25 |
| Com. Ex. 3 | CG3-1 | HT2-1 | 703 | 195 | 2.48 | −90 | +55 |
| Com. Ex. 4 | CG3-1 | 4-1 | 700 | 168 | 2.25 | −62 | +45 |
| Ex. 7 | CG4-1 | 3-1 | 702 | 44 | 1.47 | −45 | +10 |
| Ex. 8 | CG4-1 | 3-3 | 700 | 48 | 1.35 | −30 | +10 |
| Ex. 9 | CG4-1 | 3-5 | 702 | 55 | 1.62 | −25 | +30 |
| Com. Ex. 5 | CG4-1 | HT2-1 | 701 | 124 | 1.60 | −215 | +45 |
| Com. Ex. 6 | CG4-1 | 4-1 | 699 | 98 | 1.72 | −120 | +52 |
| Ex. 10 | CG4-2 | 3-1 | 700 | 46 | 1.40 | −40 | +15 |
| Ex. 11 | CG4-2 | 3-3 | 701 | 58 | 1.40 | −25 | +15 |
| Ex. 12 | CG4-2 | 3-5 | 701 | 58 | 1.65 | −30 | +30 |
| Com. Ex. 7 | CG4-2 | HT2-1 | 702 | 131 | 1.72 | −180 | +55 |
| Com. Ex. 8 | CG4-2 | 4-1 | 702 | 101 | 1.68 | −140 | +43 |
| Ex. 13 | CG4-3 | 3-1 | 704 | 47 | 1.48 | −15 | +10 |
| Ex. 14 | CG4-3 | 3-3 | 698 | 54 | 1.42 | −30 | +20 |
| Ex. 15 | CG4-3 | 3-5 | 700 | 57 | 1.68 | −25 | +25 |
| Com. Ex. 9 | CG4-3 | HT2-1 | 703 | 124 | 1.62 | −165 | +40 |
| Com. Ex. 10 | CG4-3 | 4-1 | 710 | 82 | 1.51 | −145 | +36 |

TABLE 3

| | Electric charge generating material | Electric charge transferring material | Initial electric characteristics | | | After repeated light exposure | |
|---|---|---|---|---|---|---|---|
| | | | $V_o$ | $V_r$ | $E_{1/2}$ | $\Delta V_o$ | $\Delta V_r$ |
| Ex. 16 | CG4-4 | 3-1 | 701 | 50 | 1.30 | −10 | ±0 |
| Ex. 17 | CG4-4 | 3-3 | 700 | 32 | 1.20 | −25 | +10 |
| Ex. 18 | CG4-4 | 3-5 | 699 | 40 | 1.10 | −20 | +20 |
| Com. Ex. 11 | CG4-4 | HT2-1 | 702 | 110 | 1.46 | −165 | +50 |
| Com. Ex. 12 | CG4-4 | 4-1 | 699 | 102 | 1.33 | −56 | +40 |
| Ex. 19 | CG4-5 | 3-1 | 702 | 47 | 1.50 | −20 | +10 |
| Ex. 20 | CG4-5 | 3-3 | 701 | 58 | 1.56 | −10 | +10 |
| Ex. 21 | CG4-5 | 3-5 | 701 | 57 | 1.55 | −25 | +15 |
| Com. Ex. 13 | CG4-5 | HT2-1 | 699 | 138 | 1.77 | −250 | +40 |
| Ex. 22 | CG4-6 | 3-1 | 705 | 52 | 1.27 | −35 | +25 |
| Ex. 23 | CG4-6 | 3-3 | 702 | 59 | 1.58 | −20 | +15 |
| Ex. 24 | CG4-6 | 3-5 | 700 | 56 | 1.56 | −30 | +10 |
| Com. Ex. 14 | CG4-6 | HT2-1 | 698 | 140 | 2.17 | −225 | +65 |
| Com. Ex. 15 | CG4-6 | 4-1 | 704 | 75 | 1.58 | −85 | +38 |
| Ex. 25 | CG4-7 | 3-1 | 702 | 55 | 1.25 | −40 | +20 |
| Ex. 26 | CG4-7 | 3-3 | 698 | 60 | 1.60 | −15 | +20 |
| Ex. 27 | CG4-7 | 3-5 | 699 | 58 | 1.60 | −25 | +10 |
| Com. Ex. 16 | CG4-7 | HT2-1 | 695 | 138 | 1.98 | −250 | +50 |

Examples 28 to 30 and Comparative Examples 17 and 18 (multi-layer photosensitve materials for digital light source)

First, 2.5 parts by weight of an electric charge generating material (X-type metal-free phthalocyanine represented by the formula (CG1)) and 1 part by weight of a binding resin (polyvinyl butyral) were mixed and dispersed in 15 parts by weight of a solvent (tetrahydrofuran) by means of a ball mill to prepare a coating liquid for electric charge generating layer. In turn, the coating liquid was applied on an aluminum tube serving as a conductive substrate by a dip coating method, and then dried in hot air at 110° C. for 30 minutes. Thus, an electric charge generating layer having a thickness of 0.5 µm was formed.

Subsequently, 1 part by weight of an electric charge transferring material and 1 part by weight of a binding resin (polycarbonate) were mixed and dispersed in 10 parts by weight of a solvent (tetrahydrofuran) by means of a ball mill to prepare a coating liquid for electric charge transferring layer. In turn, the coating liquid was applied on the electric charge generating layer by a dip coating method, and then dried in hot air at 110° C. for 30 minutes. Thus, an electric charge transferring layer having a thickness of 20 µm was formed. In this way, multi-layer photosensitive materials for digital light source according to Examples 28 to 30 and Comparative Examples 17 and 18 were produced.

The characteristics of the thus produced electrophotosensitive materials of Examples 28 to 30 and Comparative Examples 17 and 18 were evaluated by performing a test (III) of initial electric characteristics and a test (III) of electric characteristics after repeated light exposure, as follows.

Test (III) of initial electric characteristics

Surface potentials $V_o$ (V) of the electrophotosensitive materials of Examples 28 to 30 and Comparative Examples 17 and 18 were each measured in substantially the same manner as in the test (I) of initial electric characteristics, except that the surface thereof was charged at −700±20V.

Test (III) of electric characteristics after repeated light exposure

Differences $\Delta V_o$ (V) and $\Delta V_r$ (V) were obtained in substantially the same manner as in the test (I) of electric characteristics after repeated light exposure, except that Model LP-2080 available from MITA INDUSTRIAL CO., LTD. was used as the laser beam printer.

The electric charge transferring materials used in Examples 28 to 30 and Comparative Examples 17 and 18 and the results of the aforesaid characteristic tests are shown in Table 4.

TABLE 4

| | Electric charge generating material | Electric charge transferring material | Initial electric characteristics | | | After repeated light exposure | |
|---|---|---|---|---|---|---|---|
| | | | $V_o$ | $V_r$ | $E_{1/2}$ | $\Delta V_o$ | $\Delta V_r$ |
| Ex. 28 | CG1 | 3-1 | −702 | −15 | 0.70 | −10 | +10 |
| Ex. 29 | CG1 | 3-3 | −700 | −10 | 0.80 | −15 | +15 |
| Ex. 30 | CG1 | 3-5 | −700 | −15 | 0.75 | −20 | +15 |
| Com. Ex. 17 | CG1 | HT2-1 | −695 | −22 | 1.85 | −55 | +35 |
| Com. Ex. 18 | CG1 | 4-1 | −700 | −20 | 0.93 | −45 | +30 |

Examples 31 to 53 and Comparative Examples 19 to 32 (multi-layer photosensitive materials for analog light source)

Multi-layer photosensitive materials for analog light source were each produced in substantially the same manner as in Examples 28 to 30 and Comparative Examples 17 and 18, except that 2.5 parts by weight of the perylene pigment represented by the formula (CG3-1) or each of the bis-azo pigments represented by the formulae (CG4-1) to (CG4-7) was used as the electric charge generating material.

The characteristics of the thus produced electrophotosensitive materials of Examples 31 to 53 and Comparative Examples 19 to 32 were evaluated by performing a test (IV) of initial electric characteristics and a test (IV) of electric characteristics after repeated light exposure, as follows.

Test (IV) of initial electric characteristics

Surface potentials $V_o$ (V) of the electrophotosensitive materials of Examples 31 to 53 and Comparative Examples 19 to 32 were each measured in substantially the same manner as in the test (II) of initial electric characteristics, except that the surface thereof was charged at −700±20V.

Test (IV) of electric characteristics after repeated light exposure

Differences $\Delta V_o$ (V) and $\Delta V_r$ (V) were obtained in substantially the same manner as in the test (II) of electric characteristics after repeated light exposure, except that Model DC2556 (available from MITA INDUSTRIAL CO., LTD.) modified with negative-charging design specifications was used as the electrostatic copying machine.

The electric charge generating materials and the electric charge transferring materials used in Examples 31 to 53 and Comparative Examples 19 to 32 and the results of the aforesaid characteristic tests are shown in Tables 5 and 6.

TABLE 5

| | Electric charge generating material | Electric charge transferring material | Initial electric characteristics | | | After repeated light exposure | |
|---|---|---|---|---|---|---|---|
| | | | $V_o$ | $V_r$ | $E_{1/2}$ | $\Delta V_o$ | $\Delta V_r$ |
| Ex. 31 | CG3-1 | 3-1 | −700 | −138 | 1.84 | −50 | +10 |
| Ex. 32 | CG3-1 | 3-3 | −701 | −130 | 1.80 | −50 | +25 |
| Ex. 33 | CG3-1 | 3-5 | −700 | −129 | 1.79 | −35 | +15 |
| Com. Ex. 19 | CG3-1 | HT2-1 | −699 | −157 | 2.53 | −40 | +65 |
| Com. Ex. 20 | CG3-1 | 4-1 | −711 | −148 | 1.98 | −55 | +59 |
| Ex. 34 | CG4-1 | 3-1 | −703 | −30 | 0.46 | −55 | +15 |
| Ex. 35 | CG4-1 | 3-3 | −700 | −42 | 0.41 | −45 | +50 |
| Ex. 36 | CG4-1 | 3-5 | −701 | −42 | 0.45 | −15 | +20 |
| Com. Ex. 21 | CG4-1 | HT2-1 | −704 | −90 | 1.53 | −140 | +45 |
| Com. Ex. 22 | CG4-1 | 4-1 | −701 | −80 | 0.65 | −89 | +42 |
| Ex. 37 | CG4-2 | 3-3 | −701 | −40 | 0.39 | −45 | +52 |
| Ex. 38 | CG4-2 | 3-5 | −702 | −45 | 0.45 | −15 | +20 |
| Com. Ex. 23 | CG4-2 | HT2-1 | −697 | −125 | 1.65 | −175 | +50 |
| Com. Ex. 24 | CG4-2 | 4-1 | −705 | −68 | 0.82 | −132 | +49 |
| Ex. 39 | CG4-3 | 3-1 | −700 | −25 | 0.44 | −30 | +5 |
| Ex. 40 | CG4-3 | 3-3 | −699 | −42 | 0.38 | −41 | +50 |
| Ex. 41 | CG4-3 | 3-5 | −701 | −50 | 0.51 | −25 | +15 |
| Com. Ex. 25 | CG4-3 | HT2-1 | −701 | −104 | 1.74 | −125 | +40 |
| Com. Ex. 26 | CG4-3 | 4-1 | −699 | −75 | 0.83 | −86 | +39 |

TABLE 6

| | Electric charge generating material | Electric charge transferring material | Initial electric characteristics | | | After repeated light exposure | |
|---|---|---|---|---|---|---|---|
| | | | $V_o$ | $V_r$ | $E_{1/2}$ | $\Delta V_o$ | $\Delta V_r$ |
| Ex. 42 | CG4-4 | 3-1 | −705 | −27 | 0.36 | −45 | +5 |
| Ex. 43 | CG4-4 | 3-3 | −700 | −25 | 0.28 | −45 | +35 |
| Ex. 44 | CG4-4 | 3-5 | −702 | −22 | 0.24 | −30 | +15 |
| Com. Ex. 27 | CG4-4 | HT2-1 | −701 | −75 | 1.42 | −110 | +35 |
| Com. Ex. 28 | CG4-4 | 4-1 | −702 | −42 | 0.65 | −98 | +38 |
| Ex. 45 | CG4-5 | 3-1 | −704 | −38 | 0.45 | −50 | +20 |
| Ex. 46 | CG4-5 | 3-3 | −701 | −40 | 0.41 | −45 | +10 |
| Ex. 47 | CG4-5 | 3-5 | −699 | −55 | 0.52 | −35 | +25 |
| Com. Ex. 29 | CG4-5 | HT2-1 | −700 | −135 | 1.95 | −190 | +60 |
| Ex. 48 | CG4-6 | 3-1 | −701 | −37 | 0.62 | −50 | +35 |
| Ex. 49 | CG4-6 | 3-3 | −702 | −45 | 0.45 | −45 | +10 |
| Ex. 50 | CG4-6 | 3-5 | −701 | −54 | 0.51 | −35 | +20 |
| Com. Ex. 30 | CG4-6 | HT2-1 | −699 | −134 | 1.82 | −200 | +70 |
| Com. Ex. 31 | CG4-6 | 4-1 | −704 | −84 | 0.82 | −102 | +55 |
| Ex. 51 | CG4-7 | 3-1 | −700 | −40 | 0.50 | −45 | +25 |
| Ex. 52 | CG4-7 | 3-3 | −703 | −41 | 0.41 | −50 | +15 |
| Ex. 53 | CG4-7 | 3-5 | −700 | −55 | 0.54 | −25 | +35 |
| Com. Ex. 32 | CG4-7 | HT2-1 | −700 | −138 | 1.81 | −130 | +75 |

Examples 54 to 61 (Single-layer photosensitive materials for digital light source)

Single-layer photosensitive materials for digital light source were each produced in substantially the same manner as in Examples 1 to 3, except that 100 parts by weight of each of the phenanthrylenediamine derivatives represented by the formulae (2-1) to (2-8) was used as the electric charge transferring material, and then the aforesaid test (I) of initial electric characteristics and test (I) of electric characteristics after repeated light exposure were performed.

The electric charge transferring materials used for the electrophotosensitive materials of Examples 54 to 61 and the results of the characteristic tests are shown in Table 7.

TABLE 7

|  | Electric charge generating material | Electric charge transferring material | Initial electric characteristics | | | After repeated light exposure | |
|---|---|---|---|---|---|---|---|
|  |  |  | $V_o$ | $V_r$ | $E_{1/2}$ | $\Delta V_o$ | $\Delta V_r$ |
| Ex. 54 | CG1 | 2-1 | 699 | 48 | 1.35 | −20 | +6 |
| Ex. 55 | CG1 | 2-2 | 702 | 49 | 1.38 | −22 | +8 |
| Ex. 56 | CG1 | 2-3 | 700 | 50 | 1.39 | −18 | +7 |
| Ex. 57 | CG1 | 2-4 | 705 | 51 | 1.38 | −20 | +4 |
| Ex. 58 | CG1 | 2-5 | 701 | 46 | 1.32 | −23 | +6 |
| Ex. 59 | CG1 | 2-6 | 709 | 48 | 1.36 | −25 | +7 |
| Ex. 60 | CG1 | 2-7 | 708 | 55 | 1.41 | −31 | +8 |
| Ex. 61 | CG1 | 2-8 | 698 | 57 | 1.48 | −29 | +9 |

Examples 62 to 91 (Single-layer photosensitive materials for analog light source)

Single-layer photosensitive materials for analog light source were each produced in substantially the same manner as in Examples 4 to 27, except that 100 parts by weight of each of the phenanthrylenediamine derivatives represented by the formulae (2-1) to (2-8) was used as the electric charge transferring material, and then the aforesaid test (II) of initial-electric characteristics and test (II) of electric characteristics after repeated light exposure were performed.

The electric charge generating materials and electric charge transferring materials used for the electrophotosensitive materials of Examples 62 to 91 and the results of the characteristic tests are shown in Tables 8 and 9.

TABLE 8

|  | Electric charge generating material | Electric charge transferring material | Initial electric characteristics | | | After repeated light exposure | |
|---|---|---|---|---|---|---|---|
|  |  |  | $V_o$ | $V_r$ | $E_{1/2}$ | $\Delta V_o$ | $\Delta V_r$ |
| Ex. 62 | CG3-1 | 2-1 | 699 | 130 | 1.85 | −23 | +16 |
| Ex. 63 | CG3-1 | 2-2 | 702 | 134 | 1.84 | −25 | +18 |
| Ex. 64 | CG3-1 | 2-3 | 704 | 132 | 1.81 | −21 | +13 |
| Ex. 65 | CG3-1 | 2-5 | 710 | 133 | 1.83 | −35 | +19 |
| Ex. 66 | CG3-1 | 2-8 | 710 | 140 | 1.89 | −40 | +20 |
| Ex. 67 | CG4-1 | 2-1 | 698 | 46 | 1.51 | −30 | +12 |
| Ex. 68 | CG4-1 | 2-2 | 699 | 51 | 1.60 | −25 | +15 |
| Ex. 69 | CG4-1 | 2-3 | 705 | 49 | 1.59 | −28 | +18 |
| Ex. 70 | CG4-1 | 2-5 | 700 | 53 | 1.62 | −32 | +20 |
| Ex. 71 | CG4-1 | 2-8 | 702 | 62 | 1.69 | −34 | +13 |
| Ex. 72 | CG4-2 | 2-1 | 700 | 46 | 1.44 | −30 | +13 |
| Ex. 73 | CG4-2 | 2-2 | 699 | 48 | 1.43 | −43 | +13 |
| Ex. 74 | CG4-2 | 2-3 | 695 | 45 | 1.41 | −35 | +12 |
| Ex. 75 | CG4-2 | 2-5 | 702 | 49 | 1.43 | −29 | +18 |
| Ex. 76 | CG4-2 | 2-8 | 708 | 59 | 1.65 | −35 | +20 |

TABLE 9

|  | Electric charge generating material | Electric charge transferring material | Initial electric characteristics | | | After repeated light exposure | |
|---|---|---|---|---|---|---|---|
|  |  |  | $V_o$ | $V_r$ | $E_{1/2}$ | $\Delta V_o$ | $\Delta V_r$ |
| Ex. 77 | CG4-3 | 2-1 | 701 | 46 | 1.44 | −21 | +12 |
| Ex. 78 | CG4-3 | 2-2 | 703 | 46 | 1.43 | −38 | +13 |
| Ex. 79 | CG4-3 | 2-3 | 687 | 43 | 1.41 | −35 | +20 |
| Ex. 80 | CG4-3 | 2-5 | 709 | 48 | 1.42 | −40 | +18 |
| Ex. 81 | CG4-3 | 2-8 | 710 | 59 | 1.68 | −43 | +19 |
| Ex. 82 | CG4-4 | 2-1 | 701 | 33 | 1.51 | −12 | +8 |
| Ex. 83 | CG4-4 | 2-2 | 699 | 38 | 1.14 | −18 | +10 |
| Ex. 84 | CG4-4 | 2-3 | 703 | 39 | 1.21 | −14 | +9 |
| Ex. 85 | CG4-4 | 2-5 | 705 | 40 | 1.12 | −20 | +13 |
| Ex. 86 | CG4-4 | 2-8 | 708 | 52 | 1.36 | −13 | +18 |
| Ex. 87 | CG4-6 | 2-1 | 710 | 49 | 1.25 | −31 | +28 |
| Ex. 88 | CG4-6 | 2-2 | 712 | 51 | 1.39 | −28 | +12 |
| Ex. 89 | CG4-6 | 2-3 | 705 | 46 | 1.21 | −26 | +13 |
| Ex. 90 | CG4-6 | 2-5 | 701 | 53 | 1.33 | −32 | +18 |
| Ex. 91 | CG4-6 | 2-8 | 704 | 61 | 1.49 | −30 | +16 |

Examples 92 to 99 (multi-layer photosensitive materials for digital light source)

Multi-layer photosensitive materials for digital light source were each produced in substantially the same manner as in Examples 28 to 30, except that a coating liquid for electric charge transferring layer was prepared by using 1 part by weight of each of the phenanthrylenediamine derivatives represented by the formulae (2-1) to (2-8) as the electric charge transferring material, and then the aforesaid test (III) of initial electric characteristics and test (III) of electric characteristics after repeated light exposure were performed.

The electric charge transferring materials used for the electrophotosensitive materials of Examples 92 to 99 and the results of the characteristic tests are shown in Table 10.

TABLE 10

|  | Electric charge generating material | Electric charge transferring material | Initial electric characteristics | | | After repeated light exposure | |
|---|---|---|---|---|---|---|---|
|  |  |  | $V_o$ | $V_r$ | $E_{1/2}$ | $\Delta V_o$ | $\Delta V_r$ |
| Ex. 92 | CG1 | 2-1 | −701 | −15 | 0.71 | −15 | +11 |
| Ex. 93 | CG1 | 2-2 | −702 | −12 | 0.69 | −13 | +16 |
| Ex. 94 | CG1 | 2-3 | −700 | −11 | 0.61 | −14 | +19 |
| Ex. 95 | CG1 | 2-4 | −700 | −16 | 0.71 | −16 | +18 |
| Ex. 96 | CG1 | 2-5 | −703 | −18 | 0.74 | −20 | +13 |
| Ex. 97 | CG1 | 2-6 | −704 | −17 | 0.73 | −18 | +12 |
| Ex. 98 | CG1 | 2-7 | −701 | −17 | 0.73 | −22 | +18 |
| Ex. 99 | CG1 | 2-8 | −700 | −18 | 0.74 | −25 | +20 |

Examples 100 to 123 (Multi-layer photosensitive materials for analog light source)

Multi-layer photosensitive materials for analog light source were each produced in substantially the same manner as in Examples 31 to 53, except that 100 parts by weight of each of the phenanthrylenediamine derivatives represented by the formulae (2-1) to (2-8) were used as the electric charge transferring material, and then the aforesaid test (IV) of initial electric characteristics and test (IV) of electric characteristics after repeated light exposure were performed.

The electric charge generating materials and electric charge transferring materials used for the electrophotosensitive materials of Examples 100 to 123 and the results of the characteristic tests are shown in Tables 11 and 12.

TABLE 11

| | Electric charge generating material | Electric charge transferring material | Initial electric characteristics | | | After repeated light exposure | |
|---|---|---|---|---|---|---|---|
| | | | $V_o$ | $V_r$ | $E_{1/2}$ | $\Delta V_o$ | $\Delta V_r$ |
| Ex. 100 | CG3-1 | 2-1 | −702 | −139 | 1.90 | −40 | +10 |
| Ex. 101 | CG3-1 | 2-2 | −701 | −139 | 1.89 | −35 | +18 |
| Ex. 102 | CG3-1 | 2-3 | −689 | −131 | 1.82 | −41 | +23 |
| Ex. 103 | CG3-1 | 2-8 | −702 | −128 | 1.81 | −48 | +19 |
| Ex. 104 | CG4-1 | 2-1 | −702 | −36 | 0.48 | −53 | +15 |
| Ex. 105 | CG4-1 | 2-2 | −708 | −32 | 0.44 | −51 | +18 |
| Ex. 106 | CG4-1 | 2-3 | −700 | −38 | 0.48 | −50 | +21 |
| Ex. 107 | CG4-1 | 2-8 | −703 | −41 | 0.49 | −55 | +23 |
| Ex. 108 | CG4-2 | 2-1 | −702 | −45 | 0.49 | −48 | +18 |
| Ex. 109 | CG4-2 | 2-2 | −700 | −38 | 0.43 | −30 | +25 |
| Ex. 110 | CG4-2 | 2-3 | −706 | −42 | 0.51 | −41 | +35 |
| Ex. 111 | CG4-2 | 2-8 | −710 | −43 | 0.52 | −52 | +41 |

TABLE 12

| | Electric charge generating material | Electric charge transferring material | Initial electric characteristics | | | After repeated light exposure | |
|---|---|---|---|---|---|---|---|
| | | | $V_o$ | $V_r$ | $E_{1/2}$ | $\Delta V_o$ | $\Delta V_r$ |
| Ex. 112 | CG4-3 | 2-1 | −703 | −28 | 0.43 | −32 | +20 |
| Ex. 113 | CG4-3 | 2-2 | −700 | −49 | 0.49 | −35 | +19 |
| Ex. 114 | CG4-3 | 2-3 | −700 | −36 | 0.37 | −40 | +23 |
| Ex. 115 | CG4-3 | 2-8 | −704 | −38 | 0.39 | −51 | +35 |
| Ex. 116 | CG4-4 | 2-1 | −708 | −29 | 0.36 | −49 | +8 |
| Ex. 117 | CG4-4 | 2-2 | −701 | −32 | 0.38 | −51 | +12 |
| Ex. 118 | CG4-4 | 2-3 | −698 | −28 | 0.34 | −44 | +11 |
| Ex. 119 | CG4-4 | 2-8 | −703 | −29 | 0.32 | −52 | +19 |
| Ex. 120 | CG4-6 | 2-1 | −702 | −38 | 0.51 | −50 | +32 |
| Ex. 121 | CG4-6 | 2-2 | −706 | −35 | 0.50 | −43 | +18 |
| Ex. 122 | CG4-6 | 2-3 | −709 | −59 | 0.52 | −38 | +28 |
| Ex. 123 | CG4-6 | 2-8 | −704 | −63 | 0.63 | −39 | +29 |

As is apparent from tables 1 to 12, the electrophotosensitive materials employing the phenanthrylenediamine derivatives of the present invention are superior in the initial electric characteristics and the electric characteristics after repeated light exposure to the corresponding conventional electrophotosensitive materials.

In the photosensitive materials of Comparative Examples 2, 4, 6, 8, 10, 12, 15, 18, 20, 22, 24, 26, 28 and 31 which each employed the phenanthrylenediamine derivative represented by the formula (4-1) as the electric charge transferring material, the derivative was crystallized to such an extent that the characteristic evaluation of the photosensitive materials was not influenced thereby.

What is claimed is:

1. An electrophotosensitive material comprising a conductive substrate, and a photosensitive layer formed on the conductive substrate and containing an electric charge generating material, a binding resin, and a phenanthrylenediamine derivative as an electric charge transferring material, the phenanthrylenediamine derivative being represented by the general formula (1):

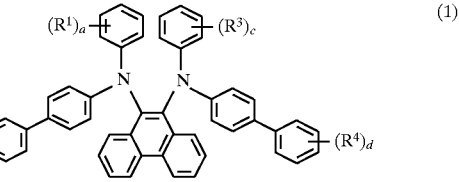

wherein $R^1$, $R^2$, $R^3$ and $R^4$ are the same or different and each represents a halogen atom, an alkyl group optionally having a substituent, an alkoxy group optionally having a substituent; or an aryl group optionally having a substituent; and a, b, c and d are the same or different and each represents an integer from 0 to 5; and the substituents are the same or different and each represents a halogen atom, an alkyl group or an alkoxy group.

2. The electrophotosensitive material as set forth in claim 1, wherein the photosensitive layer is a single-layer photosensitive layer containing the electric charge generating material, the binding resin, and the phenanthrylenediamine derivative represented by the general formula (1) as an electric charge transferring material.

3. The electrophotosensitive material as set forth in claim 1, wherein the photosensitive layer is a multi-layer photosensitive layer having an electric charge transferring layer containing the binding resin and the phenanthrylenediamine derivative represented by the general formula (1) as an electric charge transferring material and an electric charge generating layer containing the electric charge generating material.

4. The electrophotosensitive material as set forth in claim 1, the phenanthrylenediamine derivative is represented by the general formula (2):

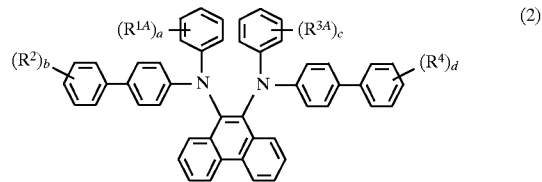

wherein $R^{1A}$ and $R^{3A}$ are different and each represents a halogen atom, an alkyl group optionally having a substituent, or an alkoxy group optionally having a substituent; $R^2$ and $R^4$ are the same or different and each represents a halogen atom, an alkyl group optionally having a substituent, an alkoxy group optionally having a substituent, or an aryl group optionally having a substituent; and a, b, c and d are the same or different and each represents an integer from 0 to 5; and the substituents are the same or different and each represents a halogen atom, an alkyl group or an alkoxy group.

5. The electrophotosensitive material as set forth in claim 1, the phenanthrylenediamine derivative is represented by the general formula (3):

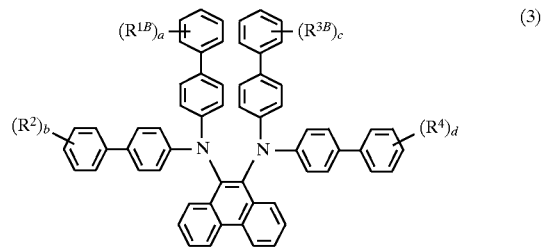

wherein $R^{1B}$, $R^2$, $R^{3B}$ and $R^4$ are the same or different and each represents a halogen atom, an alkyl group optionally having a substituent, an alkoxy group optionally having a substituent, or an aryl group optionally having a substituent; and a, b, c and d are the same or different and each represents an integer from 0 to 5; and the substituents are the same or different and each represents a halogen atom, an alkyl group or an alkoxy group.

6. The electrophotosensitive material as set forth in claim 1, the electric charge generating material is at least one selected from the group consisting of a metal-free phthalocyanine pigment, perylene pigment and bis-azo pigment.

7. The electrophotosensitive material as set forth in claim 1, wherein the binding resin is polycarbonate.

8. The electrophotosensitive material as set forth in claim 1, wherein the electric charge generating material is at least one selected from the group consisting of a metal-free phthalocyanine pigment, perylene pigment and bis-azo pigment and the binding resin is polycarbonate.

9. The electrophotosensitive material as defined in claim 1 wherein a thickness of said electric charge transferring material is from about 2 to 100 $\mu$m.

10. The electrophotosensitive material as defined in claim 9 wherein said thickness of said electric charge transferring material is from about 5 to 50 $\mu$m.

11. The electrophotosensitive material as defined in claim 1 wherein said integer is from 1–5.

12. A photosenstive material for a layer in an electrophotosensitive material, said photosensitive material comprising a binding resin and a phenanthrylenediamine derivative as an electric charge transferring material, the phenanthrylenediamine derivative being represented by the formula (1):

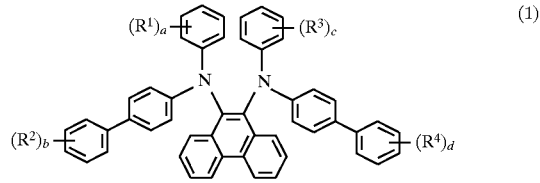

wherein $R^1$, $R^2$, $R^3$, and $R^4$ are the same or different and each represents a halogen atom, an alkyl group optionally having a substituent, an alkoxy group optionally having a substituent; or an aryl group optionally having a substituent; and a, b, c, and d are the same or different and each represents an integer from 0 to 5; and the substituents are the same or different and each represents a halogen atom, an alkyl group, or an alkoxy group.

* * * * *